United States Patent
Rowe et al.

(10) Patent No.: US 9,487,398 B2
(45) Date of Patent: *Nov. 8, 2016

(54) APPARATUS AND METHOD OF BIOMETRIC DETERMINATION USING SPECIALIZED OPTICAL SPECTROSCOPY SYSTEMS

(75) Inventors: Robert K. Rowe, Corrales, NM (US); Stephen P. Corcoran, Corrales, NM (US); Shonn P. Hendee, Albuquerque, NM (US)

(73) Assignee: HID Global Corporation, Austin, TX (US)

(*) Notice: Subject to any disclaimer, the term of this patent is extended or adjusted under 35 U.S.C. 154(b) by 986 days.

This patent is subject to a terminal disclaimer.

(21) Appl. No.: 12/181,495

(22) Filed: Jul. 29, 2008

(65) Prior Publication Data

US 2008/0304712 A1    Dec. 11, 2008

Related U.S. Application Data

(62) Division of application No. 09/874,740, filed on Jun. 5, 2001, now Pat. No. 7,890,158.

(51) Int. Cl.
*G06K 9/00* (2006.01)
*B82Y 20/00* (2011.01)
(Continued)

(52) U.S. Cl.
CPC ............... *B82Y 20/00* (2013.01); *A61B 5/117* (2013.01); *A61B 5/681* (2013.01); *B82Y 5/00* (2013.01);
(Continued)

(58) Field of Classification Search
CPC ........... G06K 9/00046; G06K 9/0012; G06K 9/2018; G06K 2009/0006; G06K 2009/00932; G06K 9/00906; G06K 9/00604; G06K 9/00885; G06K 9/00892; G06K 9/00899; G06K 9/00114; G06K 9/00268; G06K 2009/00939; G06K 9/6293; A61B 5/117; A61B 5/1172; A61B 5/1455; A61B 5/0059; A61B 5/14532; A61B 2562/0242; A61B 5/0075; A61B 5/02416; B60R 25/25; G07C 9/00158; G07C 9/00563; G01N 21/59; G01N 21/55; G01J 3/42
USPC ........................................................ 382/115
See application file for complete search history.

(56) References Cited

U.S. PATENT DOCUMENTS 3,508,830 A    4/1970   Hopkins et al.
3,910,701 A    10/1975  Henderson et al.
(Continued)

FOREIGN PATENT DOCUMENTS

EP    0 426 358 B1    5/1991
EP    0 449 335 A2    10/1991
(Continued)

OTHER PUBLICATIONS

Official Action for Japanese Patent Application No. 2003-502467 mailed on Nov. 2, 2007, 6 pages.
(Continued)

*Primary Examiner* — Kim Vu
*Assistant Examiner* — Michael Vanchy, Jr.
(74) *Attorney, Agent, or Firm* — Marsh Fischmann & Breyfogle LLP; Jonathon A. Szumny

(57) ABSTRACT

Methods and apparatuses for performing biometric determinations using optical spectroscopy of tissue. The biometric determinations that are disclosed include determination or verifications of identity, estimation of age, estimation of sex, determination of sample liveness and sample authenticity. The apparatuses disclosed are based upon discrete light sources such as light emitting diodes, laser diodes, vertical cavity surface emitting lasers, and broadband sources with multiple narrow-band optical filters. The multiple light sources are encoded in a manner that the tissue response for each source can be efficiently measured. The light sources are spaced at multiple distances from a detector to contribute differing information to the biometric determination task as do light sources with different wavelength characteristics. Apparatuses are disclosed that incorporate a spectral biometric sensor with a personal electronic device such as cellular telephones, personal digital assistants, wristwatches, electronic fobs for the purpose of providing secure biometric access to protected property.

18 Claims, 14 Drawing Sheets

(51) Int. Cl.
*A61B 5/117* (2016.01)
*B82Y 5/00* (2011.01)
*B82Y 10/00* (2011.01)
*G07C 9/00* (2006.01)
*A61B 5/00* (2006.01)

(52) U.S. Cl.
CPC ............... *B82Y 10/00* (2013.01); *G06K 9/00* (2013.01); *G07C 9/00158* (2013.01); *G07C 9/00563* (2013.01); *A61B 5/0059* (2013.01); *A61B 5/7264* (2013.01)

(56) References Cited

U.S. PATENT DOCUMENTS

| | | | |
|---|---|---|---|
| RE29,008 E | 10/1976 | Ott | |
| 4,035,083 A | 7/1977 | Woodriff et al. | |
| 4,142,797 A | 3/1979 | Astheimer | |
| 4,169,676 A | 10/1979 | Kaiser | |
| 4,260,220 A | 4/1981 | Whitehead | |
| 4,427,889 A | 1/1984 | Muller | |
| 4,537,484 A | 8/1985 | Fowler | |
| 4,598,715 A | 7/1986 | Machler et al. | |
| 4,653,880 A | 3/1987 | Sting et al. | |
| 4,654,530 A | 3/1987 | Dybwad | |
| 4,655,225 A | 4/1987 | Dahne et al. | |
| 4,656,562 A | 4/1987 | Sugino | |
| 4,657,397 A | 4/1987 | Oehler et al. | |
| 4,661,706 A | 4/1987 | Messerschmidt et al. | |
| 4,684,255 A | 8/1987 | Ford | |
| 4,712,912 A | 12/1987 | Messerschmidt | |
| 4,730,882 A | 3/1988 | Messerschmidt | |
| 4,787,013 A | 11/1988 | Sugino et al. | |
| 4,787,708 A | 11/1988 | Whitehead | |
| 4,830,496 A | 5/1989 | Young | |
| 4,853,542 A | 8/1989 | Milosevic et al. | |
| 4,857,735 A | 8/1989 | Noller | |
| 4,859,064 A | 8/1989 | Messerschmidt et al. | |
| 4,866,644 A | 9/1989 | Shenk et al. | |
| 4,867,557 A | 9/1989 | Takatani et al. | |
| 4,882,492 A | 11/1989 | Schlager | |
| 4,883,953 A | 11/1989 | Koashi et al. | |
| 4,936,680 A | 6/1990 | Henkes et al. | |
| 4,944,021 A | 7/1990 | Hoshino et al. | |
| 4,975,581 A | 12/1990 | Robinson et al. | |
| 5,015,100 A | 5/1991 | Doyle | |
| 5,019,715 A | 5/1991 | Sting et al. | |
| 5,028,787 A | 7/1991 | Rosenthal et al. | |
| 5,051,602 A | 9/1991 | Sting et al. | |
| 5,068,536 A | 11/1991 | Rosenthal | |
| 5,070,874 A | 12/1991 | Barnes et al. | |
| 5,158,082 A | 10/1992 | Jones | |
| 5,163,094 A | 11/1992 | Prokoski et al. | |
| 5,178,142 A | 1/1993 | Harjunmaa et al. | |
| 5,179,951 A | 1/1993 | Knudson | |
| 5,204,532 A | 4/1993 | Rosenthal | |
| 5,222,495 A | 6/1993 | Clarke et al. | |
| 5,222,496 A | 6/1993 | Clarke et al. | |
| 5,223,715 A | 6/1993 | Taylor | |
| 5,225,678 A | 7/1993 | Messerschmidt | |
| 5,230,702 A | 7/1993 | Lindsay et al. | |
| 5,237,178 A | 8/1993 | Rosenthal et al. | |
| 5,243,546 A | 9/1993 | Maggard | |
| 5,257,086 A | 10/1993 | Fateley et al. | |
| 5,267,152 A | 11/1993 | Yang et al. | |
| 5,268,749 A | 12/1993 | Weber et al. | |
| 5,291,560 A | 3/1994 | Daugman | |
| 5,299,570 A | 4/1994 | Hatschek | |
| 5,303,026 A | 4/1994 | Strobl et al. | |
| 5,311,021 A | 5/1994 | Messerschmidt | |
| 5,313,941 A | 5/1994 | Braig et al. | |
| 5,321,265 A | 6/1994 | Block | |
| 5,331,958 A | 7/1994 | Oppenheimer | |
| 5,348,003 A | 9/1994 | Caro | |
| 5,351,686 A | 10/1994 | Steuer et al. | |
| 5,355,880 A | 10/1994 | Thomas et al. | |
| 5,360,004 A | 11/1994 | Purdy et al. | |
| 5,361,758 A | 11/1994 | Hall et al. | |
| 5,366,903 A | 11/1994 | Lundsgaard et al. | |
| 5,372,135 A | 12/1994 | Mendelson et al. | |
| 5,379,764 A | 1/1995 | Barnes et al. | |
| 5,402,778 A | 4/1995 | Chance | |
| 5,405,315 A | 4/1995 | Khuri et al. | |
| 5,419,321 A | 5/1995 | Evans | |
| 5,435,309 A | 7/1995 | Thomas et al. | |
| 5,441,053 A | 8/1995 | Lodder et al. | |
| 5,452,723 A | 9/1995 | Wu et al. | |
| 5,459,317 A | 10/1995 | Small et al. | |
| 5,459,677 A | 10/1995 | Kowalski et al. | |
| 5,460,177 A | 10/1995 | Purdy et al. | |
| 5,483,335 A | 1/1996 | Tobias | |
| 5,494,032 A | 2/1996 | Robinson et al. | |
| 5,505,726 A | 4/1996 | Meserol | |
| 5,507,723 A | 4/1996 | Keshaviah | |
| 5,515,847 A | 5/1996 | Braig et al. | |
| 5,518,623 A | 5/1996 | Keshaviah et al. | |
| 5,523,054 A | 6/1996 | Switalski et al. | |
| 5,533,509 A | 7/1996 | Koashi et al. | |
| 5,537,208 A | 7/1996 | Bertram et al. | |
| 5,539,207 A | 7/1996 | Wong et al. | |
| 5,552,997 A | 9/1996 | Massart | |
| 5,559,504 A | 9/1996 | Itsumi et al. | |
| 5,596,992 A | 1/1997 | Haaland et al. | |
| 5,606,164 A | 2/1997 | Price et al. | |
| 5,630,413 A | 5/1997 | Thomas et al. | |
| 5,636,633 A | 6/1997 | Messerschmidt et al. | |
| 5,655,530 A | 8/1997 | Messerschmidt | |
| 5,672,864 A | 9/1997 | Kaplan | |
| 5,672,875 A | 9/1997 | Block et al. | |
| 5,677,762 A | 10/1997 | Ortyn et al. | |
| 5,681,273 A | 10/1997 | Brown | |
| 5,708,593 A | 1/1998 | Saby et al. | |
| 5,719,399 A | 2/1998 | Alfano et al. | |
| 5,719,950 A * | 2/1998 | Osten ................ | A61B 5/0205 340/5.82 |
| 5,724,268 A | 3/1998 | Sodickson et al. | |
| 5,737,439 A | 4/1998 | Lapsley et al. | |
| 5,743,262 A | 4/1998 | Lepper, Jr. et al. | |
| 5,747,806 A | 5/1998 | Khalil | |
| 5,750,994 A | 5/1998 | Schlager | |
| 5,751,835 A | 5/1998 | Topping et al. | |
| 5,761,330 A | 6/1998 | Stoianov et al. | |
| 5,782,755 A | 7/1998 | Chance et al. | |
| 5,792,050 A | 8/1998 | Alam et al. | |
| 5,792,053 A | 8/1998 | Skladnev et al. | |
| 5,793,881 A | 8/1998 | Stiver et al. | |
| 5,796,858 A | 8/1998 | Zhou et al. | |
| 5,808,739 A | 9/1998 | Turner et al. | |
| 5,818,048 A | 10/1998 | Sodickson et al. | |
| 5,823,951 A | 10/1998 | Messerschmidt et al. | |
| 5,828,066 A | 10/1998 | Messerschmidt | |
| 5,830,132 A * | 11/1998 | Robinson ................ | 600/310 |
| 5,830,133 A | 11/1998 | Osten et al. | |
| 5,850,623 A | 12/1998 | Carman, Jr. et al. | |
| 5,853,370 A | 12/1998 | Chance et al. | |
| 5,857,462 A | 1/1999 | Thomas et al. | |
| 5,860,421 A | 1/1999 | Eppstein et al. | |
| 5,867,265 A * | 2/1999 | Thomas ................ | 356/328 |
| 5,886,347 A | 3/1999 | Inoue et al. | |
| 5,902,033 A | 5/1999 | Levis et al. | |
| 5,914,780 A | 6/1999 | Turner et al. | |
| 5,929,443 A | 7/1999 | Alfano et al. | |
| 5,933,792 A | 8/1999 | Andersen et al. | |
| 5,935,062 A | 8/1999 | Messerschmidt et al. | |
| 5,945,676 A | 8/1999 | Khalil | |
| 5,949,543 A | 9/1999 | Bleier et al. | |
| 5,957,841 A | 9/1999 | Maruo et al. | |
| 5,961,449 A | 10/1999 | Toida et al. | |
| 5,963,319 A | 10/1999 | Jarvis et al. | |
| 5,987,346 A | 11/1999 | Benaron et al. | |
| 5,999,637 A | 12/1999 | Toyoda et al. | |
| 6,005,722 A | 12/1999 | Butterworth et al. | |
| 6,016,435 A | 1/2000 | Maruo et al. | |
| 6,025,597 A | 2/2000 | Sterling et al. | |
| 6,026,314 A | 2/2000 | Amerov et al. | |

(56) References Cited

U.S. PATENT DOCUMENTS

| | | | |
|---|---|---|---|
| 6,028,773 A | 2/2000 | Hundt | |
| 6,031,609 A | 2/2000 | Funk et al. | |
| 6,034,370 A | 3/2000 | Messerschmidt | |
| 6,040,578 A | 3/2000 | Malin et al. | |
| 6,041,247 A | 3/2000 | Weckstrom et al. | |
| 6,041,410 A * | 3/2000 | Hsu et al. | 713/186 |
| 6,043,492 A | 3/2000 | Lee et al. | |
| 6,044,285 A | 3/2000 | Chaiken et al. | |
| 6,045,502 A | 4/2000 | Eppstein et al. | |
| 6,046,808 A | 4/2000 | Fateley | |
| 6,049,727 A | 4/2000 | Crothall | |
| 6,056,738 A | 5/2000 | Marchitto et al. | |
| 6,057,925 A | 5/2000 | Anthon | |
| 6,061,581 A | 5/2000 | Alam et al. | |
| 6,061,582 A | 5/2000 | Small et al. | |
| 6,066,847 A | 5/2000 | Rosenthal | |
| 6,069,689 A | 5/2000 | Zeng et al. | |
| 6,070,093 A | 5/2000 | Oosta et al. | |
| 6,073,037 A | 6/2000 | Alam et al. | |
| 6,088,605 A | 7/2000 | Griffith et al. | |
| 6,088,607 A | 7/2000 | Diab et al. | |
| 6,097,035 A | 8/2000 | Belongie et al. | |
| 6,100,811 A | 8/2000 | Hsu et al. | |
| 6,115,484 A | 9/2000 | Bowker et al. | |
| 6,115,673 A | 9/2000 | Malin et al. | |
| 6,122,042 A * | 9/2000 | Wunderman | A61B 1/05 356/343 |
| 6,122,394 A | 9/2000 | Neukermans et al. | |
| 6,122,737 A | 9/2000 | Bjorn et al. | |
| 6,125,192 A | 9/2000 | Bjorn et al. | |
| 6,141,101 A | 10/2000 | Bleier et al. | |
| 6,147,749 A | 11/2000 | Kubo et al. | |
| 6,148,094 A | 11/2000 | Kinsella | |
| 6,152,876 A | 11/2000 | Robinson et al. | |
| 6,154,658 A | 11/2000 | Caci | |
| 6,157,041 A | 12/2000 | Thomas et al. | |
| 6,159,147 A | 12/2000 | Lichter et al. | |
| 6,172,743 B1 | 1/2001 | Kley et al. | |
| 6,175,407 B1 | 1/2001 | Sartor | |
| 6,181,414 B1 | 1/2001 | Raz et al. | |
| 6,181,958 B1 | 1/2001 | Steuer et al. | |
| 6,188,781 B1 | 2/2001 | Brownlee | |
| 6,212,424 B1 | 4/2001 | Robinson | |
| 6,226,541 B1 | 5/2001 | Eppstein et al. | |
| 6,230,034 B1 | 5/2001 | Messerschmidt et al. | |
| 6,240,306 B1 | 5/2001 | Rohrscheib et al. | |
| 6,240,309 B1 | 5/2001 | Yamashita et al. | |
| 6,241,663 B1 | 6/2001 | Wu et al. | |
| 6,256,523 B1 | 7/2001 | Diab et al. | |
| 6,272,367 B1 | 8/2001 | Chance | |
| 6,280,381 B1 | 8/2001 | Malin et al. | |
| 6,282,303 B1 | 8/2001 | Brownlee | |
| 6,285,895 B1 | 9/2001 | Ristolainen et al. | |
| 6,292,576 B1 | 9/2001 | Brownlee | |
| 6,301,815 B1 * | 10/2001 | Sliwa | 42/70.01 |
| 6,304,767 B1 | 10/2001 | Soller et al. | |
| 6,307,633 B1 | 10/2001 | Mandella et al. | |
| 6,309,884 B1 | 10/2001 | Cooper et al. | |
| 6,317,507 B1 | 11/2001 | Dolfing et al. | |
| 6,324,310 B1 | 11/2001 | Brownlee | |
| 6,327,376 B1 * | 12/2001 | Harkin | 382/124 |
| 6,330,346 B1 | 12/2001 | Peterson et al. | |
| 6,353,226 B1 | 3/2002 | Khalil et al. | |
| 6,404,904 B1 | 6/2002 | Einighammer et al. | |
| 6,483,929 B1 | 11/2002 | Murakami et al. | |
| 6,504,614 B1 | 1/2003 | Messerschmidt et al. | |
| 6,560,352 B2 | 5/2003 | Rowe et al. | |
| 6,574,490 B2 | 6/2003 | Abbink et al. | |
| 6,628,809 B2 | 9/2003 | Rowe et al. | |
| 6,741,729 B2 | 5/2004 | Bjorn et al. | |
| 6,799,275 B1 | 9/2004 | Bjorn | |
| 6,816,605 B2 | 11/2004 | Rowe et al. | |
| 7,890,158 B2 | 2/2011 | Rowe et al. | |
| 2001/0056237 A1 | 12/2001 | Cane et al. | |
| 2002/0009213 A1 * | 1/2002 | Rowe et al. | 382/115 |
| 2002/0091937 A1 * | 7/2002 | Ortiz | 713/200 |
| 2002/0138768 A1 | 9/2002 | Murakami et al. | |
| 2002/0171834 A1 | 11/2002 | Rowe et al. | |
| 2002/0183624 A1 | 12/2002 | Rowe et al. | |
| 2003/0078504 A1 | 4/2003 | Rowe | |
| 2004/0047493 A1 | 3/2004 | Rowe et al. | |
| 2004/0240712 A1 | 12/2004 | Rowe et al. | |

FOREIGN PATENT DOCUMENTS

| | | | |
|---|---|---|---|
| EP | 0 573 137 A2 | 12/1993 | |
| EP | 0 631 137 A2 | 12/1994 | |
| EP | 0 670 143 A1 | 9/1995 | |
| EP | 0 681 166 A1 | 11/1995 | |
| EP | 0 757 243 A1 | 2/1997 | |
| EP | 0 788 000 A2 | 8/1997 | |
| EP | 0 801 297 A1 | 10/1997 | |
| EP | 0 836 083 A1 | 4/1998 | |
| EP | 0 843 986 A2 | 5/1998 | |
| EP | 0 869 348 A2 | 10/1998 | |
| EP | 0 280 418 A1 | 2/1999 | |
| EP | 0 897 164 A2 | 2/1999 | |
| EP | 0 897 691 A2 | 2/1999 | |
| EP | 0 317 121 B1 | 5/1999 | |
| EP | 0 924 656 A2 | 6/1999 | |
| EP | 0 982 583 A1 | 3/2000 | |
| EP | 0 990 945 A1 | 4/2000 | |
| EP | 0 936 762 B9 | 10/2005 | |
| EP | 0 941 694 B1 | 8/2007 | |
| JP | 3016160 | 1/1991 | |
| JP | 08138046 A * | 5/1996 | G06T 7/00 |
| JP | 9510636 A | 10/1997 | |
| JP | 10-127585 | 5/1998 | |
| JP | 11-244266 A | 9/1999 | |
| JP | 2001-101309 A | 4/2001 | |
| JP | 2001-112742 | 4/2001 | |
| WO | WO 92/00513 A1 | 1/1992 | |
| WO | WO 92/17765 A1 | 10/1992 | |
| WO | WO 93/00855 A1 | 1/1993 | |
| WO | WO 93/07801 A1 | 4/1993 | |
| WO | WO 95/22046 A1 | 8/1995 | |
| WO | WO 95/26013 A1 | 9/1995 | |
| WO | WO 97/23159 A1 | 7/1997 | |
| WO | WO 97/27800 A1 | 8/1997 | |
| WO | WO 97/28437 A1 | 8/1997 | |
| WO | WO 97/28438 A1 | 8/1997 | |
| WO | WO 98/01071 A1 | 1/1998 | |
| WO | WO 98/37805 A1 | 9/1998 | |
| WO | WO 98/40723 A1 | 9/1998 | |
| WO | WO 99/09395 A1 | 2/1999 | |
| WO | WO 99/37203 A2 | 7/1999 | |
| WO | WO 99/43255 A1 | 9/1999 | |
| WO | WO 99/46731 A1 | 9/1999 | |
| WO | WO 99/55222 A1 | 11/1999 | |
| WO | WO 99/56616 A1 | 11/1999 | |
| WO | WO 00/30530 | 6/2000 | |
| WO | WO 01/15596 A1 | 3/2001 | |
| WO | WO 01/18332 A1 | 3/2001 | |
| WO | WO 01/20538 | 3/2001 | |
| WO | WO 01/27882 A2 | 4/2001 | |
| WO | WO 01/52180 A1 | 7/2001 | |
| WO | WO 01/52726 A1 | 7/2001 | |
| WO | WO 01/53805 A1 | 7/2001 | |
| WO | WO 02/084605 A2 | 10/2002 | |
| WO | WO 02/099393 A2 | 12/2002 | |
| WO | WO 2004/068388 A2 | 8/2004 | |
| WO | WO 2004/068394 A1 | 8/2004 | |

OTHER PUBLICATIONS

Anderson, C. E. et al., "Fundamentals of Calibration Transfer Through Procrustes Analysis," Appln. Spectros., vol. 53, No. 10 (1999) p. 1268-1276.

Ashbourn, Julian, Biometrics; Advanced Identity Verification, Springer, 2000, pp. 63-64).

Bantle, John P. et al., "Glucose Measurement in Patients With Diabetes Mellitus With Dermal Interstitial Fluid," Mosby-Year Book, Inc., 9 pages, 1997.

(56) References Cited

OTHER PUBLICATIONS

Berkoben, Michael S. et al., "Vascular Access for Hemodialysis," Clinical Dialysis, Third Edition, pp. 2 cover pages and 26-45, 1995.
Blank, T.B. et al., "Transfer of Near-Infrared Multivariate Calibrations Without Standards," Anal. Chem., vol. 68 (1996) p. 2987.
Bleyer, Anthony J. et al., "The Costs of Hospitalizations Due to Hemodialysis Access Management," Nephrology News & Issues, pp. 19, 20 and 22, Jan. 1995.
Brasunas John C. et al., "Uniform Time-Sampling Fourier Transform Spectroscopy," Applied Optics, vol. 36, No. 10, Apr. 1, 1997, pp. 2206-2210.
Brault, James W., "New Approach to High-Precision Fourier Transform Spectrometer Design," Applied Optics, Vo. 35, No. 16, Jun. 1, 1996, pp. 2891-2896.
Brochure entitled "Improve the Clinical Outcome of Every Patient", In Line Diagnostics, published on or before Oct. 30, 1997, 2 pages.
Cassarly, W.J. et al., "Distributed Lighting Systems: Uniform Light Delivery," Source Unknown, pp. 1698-1702.
Chang, Chong-Min et al., "An Uniform Rectangular Illuminating Optical System for Liquid Crystal Light Valve Projectors," Euro Display '96 (1996) pp. 257-260.
Coyne, Lawrence J. et al., "Distributive Fiber Optic couplers Using Rectangular Lightguides as Mixing Elements," (Information Gatekeepers, Inc. Brookline, MA, 1979) pp. 160-164.
Daugirdas, JT et al., "Comparison of Methods to Predict the Equilibrated Kt/V (eKt/V) In The Hemo Study," National Institutes of Health, pp. 1-28, Aug. 20, 1996.
de Noord, Onno E., "Multivariate Calibration Standardization," Chemometrics and intelligent Laboratory Systems 25, (1994) pp. 85-97.
Demos, S. G. et al., "Optical Fingerprinting Using Polarisation Contrast Improvement," Electronics Letters, vol. 33, No. 7, pp. 582-584, Mar. 27, 1997.
Depner, Thomas A. et al., "Clinical Measurement of Blood Flow in Hemodialysis Access Fistulae and Grafts by Ultrasound Dilution," Division of Nephrology, University of California, pp. M745-M748, published on or before Oct. 30, 1997.
Despain, Alvin M. et al., "A Large-Aperture Field-Widened Interferometer-Spectrometer for Airglow Studies," Aspen International Conference on Fourier Spectroscopy, 1970, pp. 293-300.
Faber, Nicolaas, "Multivariate Sensitivity for the Interpretation of the Effect of Spectral Pretreatment Methods on Near-Infrared Calibration Model Predictions," Analytical Chemistry, vol. 71, No. 3, Feb. 1, 1999, pp. 557-565.
Fresenius USA, "Determination of Delivered Therapy Through Measurement of Effective Clearance," 2 pages, Dec. 1994.
Geladi, Paul et al., A Multivariate NIR Study of Skin Alterations in Diabetic Patients as Compared to Control Subj ects, J. Near Infrared Spectrosc., vol. 8 (2000) pp. 217-227.
Haaland, David M. et al. "Reagentless Near-Infrared Determination of Glucose in Whole Blood Using Multivariate Calibration," Applied Spectroscopy, vol. 46, No. 10 (1992) pp. 1575-1578.
Hakim, Raymond M. et al., "Effects of Dose of Dialysis on Morbidity and Mortality," American Journal of Kidney Diseases, vol. 23, No. 5, pp. 661-669, May 1994.
Harwit, M. et al., "Chapter 5—Instrumental Considerations" Hadamard Transform Optics, Academic Press (1979) pp. 109-145.
Heise H. Michael et al., "Near-Infrared Reflectance Spectroscopy for Noninvasive Monitoring of Metabolites," Clin. Chem. Lab. Med. 2000, 38(2) (2000) pp. 137-145.
Heise, H.M. "Non-Invasive Monitoring of Metabolites Using Near Infrared Spectroscopy: State of the Art," Horm. Metab. Res., vol. 28 (1996) pp. 527-534.
Heise, H.M. et al., "Near Infrared Spectrometric Investigation of Pulsatile Blood Flow for Non Invasive Metabolite Monitoring," CP430, Fourier Transform Spectroscopy: 11th International Conference, (1998) pp. 282-285.
Heise, H.M. et al., "Noninvasive Blood Glucose Sensors Based on Near-Infrared Spectroscopy," Artif Organs, vol. 18, No. 6 (1994) pp. 1-9.

Hopkins, George W. et al., "In-vivo NIR Diffuse-reflectance Tissue Spectroscopy of Human Subjects," SP1E, vol. 3597, Jan. 1999, pp. 632-641.
Jacobs, Paul et al., "A Disposable Urea Sensor for Continuous Monitoring of Hemodialysis Efficiency," ASAIO Journal, pp. M353-M358, 1993.
Jagemann, Kay-Uwe et al. "Application of Near-Infrared Spectroscopy for Non-Invasive Determination of Blood/Tissue Glucose Using Neural Networks," Zeitschrift for Physikalische Chemie, Bd.191, S. 179-190 (1995).
Keshaviah, Prakash R. et al., "On-Line Monitoring of the Delivery of the Hemodialysis Prescription," Pediatric Nephrology, vol. 9, pp. S2-S8, 1995.
Khalil, Omar S., "Spectroscopic and Clinical Aspects of Noninvasive Glucose Measurements," Clinical Chemistry, 45:2 (1999) pp. 165-177.
Kohl, Matthias et al., "The Influence of Glucose Concentration Upon the Transport of Light in Tissue-simulating Phantoms," Phys. Med. Biol., vol. 40 (1995) pp. 1267-1287.
Korte, E.H. et al., "Infrared Diffuse Reflectance Accessory for Local Analysis on Bulky Samples," Applied Spectroscopy, vol. 42, No. 1, Jan. 1988, pp. 38-43.
Krivitski, Nikolai M., "Theory and Validation of Access Flow Measurement by Dilution Technique During Hemodialysis," Kidney International, vol. 48, pp. 244-250, 1995.
Kumar, G. et al., "Optimal Probe Geometry for Near-Infrared Spectroscopy of Biological Tissue," Applied Spectroscopy, vol. 36 (1997) p. 2286.
Lorber, Avraham et al., "Local Centering in Multivariate Calibration," Journal of Chemometrics, vol. 10 (1996) pp. 215-220.
Lorber, Avraham et al., "Net Analyte Signal Calculation in Multivariate Calibration," Analytical Chemistry, vol. 69, No. 8, Apr. 15, 1997, pp. 1620-1626.
Marbach, R. et al. "Noninvasive Blood Glucose Assay by Near-Infrared Diffuse Reflectance Spectroscopy of the Human Inner Lip," Applied Spectroscopy, vol. 47, No. 7 (1993) pp. 875-881.
Marbach, R. et al. "Optical Diffuse Reflectance Accessory for Measurements of Skin Tissue by Near-Infrared Spectroscopy," Applied Optics, vol. 34, No. 4, Feb. 1, 1995, pp. 610-621.
Marbach, Ralf, "Measurement Techniques for IR Spectroscopic Blood Glucose Determination," Fortschritt Bericht, Series 8: Measurement and Control Technology, No. 346, pp. cover and 1-158, Mar. 28, 1994.
Mardia, K.V. et al., "Chapter 11—Discriminant Analysis," Multivariate Analysis, pp. 2 cover pp. and 300-325, 1979.
Martens, Harald et al., Updating Multivariate Calibrations of Process NIR Instruments, Adv. Instru. Control (1990) pp. 371-381.
McIntosh, Bruce C. et al. "Quantitative Reflectance Spectroscopy in the Mid-IR", 16' Annual FACSS Conference, Oct. 1989.
Nichols, Michael G. et al., "Design and Testing of a White-Light, Steady-State Diffuse Reflectance Spectrometer for Determination of Optical Properties of Highly Scattering Systems," Applied Optics, vol. 36, No. 1, pp. 93-104, Jan. 1, 1997.
Offner, A., "New Concepts in Projection Mask Aligners," Optical Engineering, vol. 14, No. 2, Mar.-Apr. 1975, pp. 130-132.
Osborne, B.G. et al., "Optical Matching of Near Infrared Reflectance Monochromator Instruments for the Analysis of Ground and Whole Wheat," J. Near Infrared Spectrosc., vol. 7 (1999) p. 167.
Ozdemir, d. et al., "Hybrid Calibration Models: An Alternative to Calibration Transfer," Applied Spectros., vol. 52, No. 4, 1998, pp. 599-603.
Powell, J.R. et al, "An Algorithm for the Reproducible Spectral Subtraction of Water from the FT IR Spectra of Proteins in Dilute Solutions and Adsorbed Monolayers," Applied Spectroscopy, vol. 40, No. 3 (1986) pp. 339-344.
Ripley, B. D., "Chapter 3—Linear Discriminant Analysis," Pattern Recognition and Neural Networks, pp. 3 cover pp. and 91-120, 1996.
Robinson, M. Ries et al., "Noninvasive Glucose Monitoring in Diabetic Patients: A Preliminary Evaluation," Clinical Chemistry, vol. 38, No. 9 (1992) pp. 1618-1622.

(56) References Cited

OTHER PUBLICATIONS

Ronco, C. et al., "On-Line Urea Monitoring : A Further Step Towards Adequate Dialysis Prescription and Delivery," The International Journal of Artificial Organs, vol. 18, No. 9, pp. 534-543, 1995.

Royston, David D. et al., "Optical Properties of Scattering and Absorbing Materials Used in the Development of Optical Phantoms at 1064 NM," Journal of Biomedical Optics, vol. 1, No. 1, Jan. 1996, pp. 110-116.

Rutan, Sarah C. et al., "Correction for Drift in Multivariate Systems Using the Kalman Filter," Chemometrics and Intelligent Laboratory Systems 35, (1996) pp. 199-211.

Salit, M.L. et al., "Heuristic and Statistical Algorithms for Automated Emission Spectral Background Intensity Estimation," Applied Spectroscopy, vol. 48, No. 8 (1994) pp. 915-925.

Saptari, Vidi Alfandi, "Analysis, Design and Use of a Fourier-Transform Spectrometer for Near Infrared Glucose Absorption Measurement," (Massachusetts Institute of Technology, 1999) pp. 1-76.

Schmitt, J.M. et al., "Spectral Distortions in Near-Infrared Spectroscopy of Turbid Materials," Applied Spectroscopy, No. 50 (1996) p. 1066.

Service, F. John et al., "Dermal Interstitial Glucose as an Indicator of Ambient Glycemia," Diabetes Care, vol. 20, No. 9, 8 pages, Aug. 1997.

Sherman, Richard A., "Chapter 4—Recirculation in the Hemodialysis Access," Principles and Practice of Dialysis, pp. 2 cover pp. and 38-46, 1994.

Sherman, Richard A., "The Measurement of Dialysis Access Recirculation," American Journal of Kidney Diseases, vol. 22, No. 4, pp. 616-621, Oct. 1993.

Shroder, Robert, Slides from MicroPac Forum Presentation, Current performance results, May 11, 2000; slides 2,4,14.

Sjoblom, J. et al., "An Evaluation of Orthogonal Signal correction Applied to Calibration Transfer of Near Infrared Spectra," Chemom & Intell Lab. Systems, vol. 44 (1998) p. 229-244.

Steel, W.H., "Interferometers for Fourier Spectroscopy," Aspen International Conference on Fourier Spectroscopy, (1970) pp. 43-53.

Sternberg R.S. et al., "A New Type of Michelson Interference Spectrometer," Sci. Instrum., vol. 41 (1964) pp. 225-226.

Steuer, Robert R. et al., "A New Optical Technique for Monitoring Hematocrit and Circulating Blood Volume: Its Application in Renal Dialysis," Dialysis & Transplantation, vol. 22, No. 5, pp. 260-265, May 1993.

Stork, Chris L. et al., "Weighting Schemes for Updating Regression Models—A Theoretical Approach," Chemometrics and Intelligent Laboratory Systems 48, (1999) pp. 151-166.

Sum, Stephen T. et al., "Standardization of Fiber-Optic Probes for Near-Infrared Multivariate Calibrations," Applied Spectroscopy, vol. 52, No. 6 (1998) pp. 869-877.

Swierenga, H. et al., "Comparison of Two Different Approaches Toward Model Transferability in NIR Spectroscopy," Applied Spectroscopy, vol. 52, No. 1 (1998) pp. 7-16.

Swierenga, H. et al., "Improvement of PLS Model Transferability by Robust Wavelength Selection," Chemometrics and Intelligent Laboratory Systems, vol. 41 (1998) pp. 237-248.

Swierenga, H. et al., "Strategy for Constructing Robust Multivariate Calibration Models," Chemometrics and Intelligent Laboratory Systems, vol. 49, (1999) pp. 1-17.

Teijido, J.M. et al., "Design of a Non-conventional Illumination System Using a Scattering Light Pipe," SPIE, Vo. 2774 (1996) pp. 747-756.

Teijido, J.M. et al., "Illumination Light Pipe Using Micro-Optics as Diffuser," SPIE, vol. 2951 (1996) pp. 146-155.

Thomas, Edward V. et al., "Development of Robust Multivariate Calibration Models," Technometrics, vol. 42, No. 2, May 2000, pp. 168-177.

Tipler, Paul A., Physics, Second Edition, Worth Publishers, Inc., Chapter 34, Section 34-2, Nov. 1983, pp. 901-908.

Wang, Y-D. et al., "Calibration Transfer and Measurement Stability of Near-Infrared Spectrometers," Appl. Spectros., vol. 46, No. 5 (1992) pp. 764-771.

Wang, Y-D. et al., "Improvement of Multivariate Calibration Through Instrument Standardization," Anal. Chem., vol. 64 (1992) pp. 562-564.

Wang, Z., "Additive Background Correction in Multivariate Instrument Standardization," Anal. Chem., vol. 67 (1995) pp. 2379-2385.

Ward, Kenneth J. et al., "Post-Prandial Blood Glucose Determination by Quantitative Mid-Infrared Spectroscopy," Applied Spectroscopy, vol. 46, No. 6 (1992) pp. 959-965.

Webb, Paul, "Temperatures of Skin, Subcutaneous Tissue, Muscle and Core in Resting Men in Cold, Comfortable and Hot Conditions," European Journal of Applied Physiology, vol. 64, pp. 471-476, 1992.

Whitehead, L.A. et al., "High-efficiency Prism Light Guides with Confocal Parabolic Cross Sections," Applied Optics, vol. 37, No. 22 (1998) pp. 5227-5233.

Zavala, Albert et al., "Using Fingerprint Measures to Predict Other Anthropometric Variables," Human Factors, vol. 17, No. 6, pp. 591-602, 1975.

Official Action for Japanese Patent Application No. 2008-237232, mailed on Apr. 25, 2011, 8 pages.

\* cited by examiner

APPARATUS AND METHOD OF BIOMETRIC DETERMINATION USING SPECIALIZED OPTICAL SPECTROSCOPY SYSTEMS

CROSS-REFERENCES TO RELATED APPLICATIONS

This application is a division of U.S. patent application Ser. No. 09/874,740, filed Jun. 5, 2001, entitled "Apparatus and Method of Biometric Determination Using Specialized Optical Spectroscopy Systems" ("the parent application") which is incorporated herein by reference for all purposes. The parent application is related to U.S. patent application Ser. No. 09/832,534, filed Apr. 11, 2001, entitled "Apparatus and Method of Biometric Identification or Verification of Individuals using Optical Spectroscopy", which is a continuation-in-part of U.S. patent application Ser. No. 09/415,594, filed Oct. 8, 1999, entitled "Apparatus and Method for Identification of Individuals by Near-Infrared Spectrum"; which is related to U.S. patent application Ser. No. 09/174,812, filed Oct. 19, 1998, entitled "Method for Non-Invasive Analyte Measurement with Improved Optical Interface"; and U.S. patent application Ser. No. 08/871,366, filed Jun. 9, 1997, entitled "Diffuse Reflectance Monitoring Apparatus", all assigned to the same assignee as the present application, and the disclosures of which are incorporated herein by reference.

TECHNICAL FIELD

This present invention relates generally to methods and systems for performing biometric determinations of individuals utilizing optical spectra of tissue. More specifically, the invention relates to methods and systems for determining or verifying identity, determining or verifying age, determining or verifying sex, and determining or verifying liveness and authenticity of the sample being measured. The present invention discloses methods and systems for gathering optical information about the tissue using a combination of wavelengths and source-detector separations. The present invention discloses a family of compact, special-purpose optical sensors operating in the near-ultraviolet, visible, and near-infrared spectral regions that are suitable for a variety of biometric determination tasks. The sensors can be used in stand-alone, dedicated applications or can be incorporated in a variety of personal devices such as cellular telephones, personal digital assistants, wrist watches, or electronic fobs to provide personal biometric security to protect access to a variety of protected property.

BACKGROUND OF THE INVENTION

Biometric determination is generally defined as the process of measuring and using one or more physical or behavioral features or attributes to gain information about identity, age, or sex of a person, animal, or other biological entity. As well, in order to ensure security, the biometric determination task may include further tasks that ensure that the sample being measured is authentic and being measured on a living being. This latter test is referred to as a determination of liveness.

There are two common modes in which biometric determinations of identity occur: one-to-many (identification) and one-to-one (verification). One-to-many identification attempts to answer the question of, "do I know you?" The biometric measurement device collects a set of biometric data and from this information alone it assesses whether the person is a previously seen ("authorized") individual. Systems that perform the one-to-many identification task, such as the FBI's Automatic Fingerprint Identification System (AFIS), are generally very expensive ($10 million or more) and require many minutes to detect a match between an unknown sample and a large database containing hundreds of thousands or millions of entries. The one-to-one mode of biometric analysis answers the question of, "are you who you say you are?" This mode is used in cases where an individual makes a claim of identity using a user name, a personal identification number (PIN) or other code, a magnetic card, or other means, and the device collects a set of biometric data which it uses to confirm the identity of the person.

Although in general the one-to-many identification task is more difficult than one-to-one, the two tasks become the same as the number of recognized or authorized users for a given biometric device decreases to just a single individual. Situations in which a biometric identification task has only a small number of entries in the authorization database are quite common. For example, biometric access to a residence, to a personal automobile, to a personal computer, to a cellular telephone, and to other such personal devices typically require an authorization database of just a few people.

Biometric identification and verification is useful in many applications. Examples include verifying identity prior to activating machinery or gaining entry to a secure area. Another example would be identification of an individual for matching that individual to records on file for that individual, such as for matching hospital patient records especially when the individual's identity is unknown. Biometric identification is also useful to match police records at the time a suspect is apprehended, but true identity of the suspect is not known. Additional uses of biometric identification or verification include automotive keyless start and entry applications, secure computer and network access applications, automated financial transaction applications, authorized handgun use applications, and time-and-attendance applications. In general, protected property will be the term used to describe all of the goods, places, services, and information that may require biometric authorization to access.

Current methods for biometric identification are manifold, but some of the most common techniques include fingerprint pattern matching, facial recognition, hand geometry, iris scanning, and voice recognition. Each of these technologies addresses the need for biometric identification to some extent. However, due to cost, performance, or other issues, each of the existing methods has advantages and disadvantages relative to the other technologies.

There are currently many personal electronic devices that are used to gain access to protected property but that do not include any biometric capability. For example, electronic fobs are commonly used to gain entry to automobiles and to activate commercial and residential alarm systems. Wristwatches such as the Swatch Access models can be used to purchase and download codes that allow easy entry to ski areas and other for-pay recreational sites. A wristwatch being sold by Xyloc permits access to computers, printers, networks, or other properly equipped hardware and systems when the watch is in the vicinity of the protected system. A small electronic device known as an iButton sold by Dallas Semiconductor can be put into a ring, key fob, wallet, watch, metal card or badge, that a person can carry and use to gain access to properly equipped doors and other protected systems. However, an unauthorized user can gain access to any of the property protected by these systems by simply obtaining a device from an authorized user. These devices do not have the capability to distinguish between authorized and unauthorized users and will work for anyone who possesses them. This deficiency represents a major security concern.

In U.S. Pat. No. 6,041,410, Hsu et al. disclose a personal identification fob that employs fingerprint data. This system is specified to contain memory to hold the fingerprint image, an image correlater, a communication means employing a cyclic redundancy code, and a "door" that is controlled by the biometric system and allows access to protected property. Hsu et al. generalize "door" as a means to access protected property including a building, a room, an automobile, and a financial account. The method disclosed relates to a door that protects property and its interaction with the fob, including a "wake-up" message and a series of steps to collect the biometric data and compare it with reference data, determining a match, and then actuating the device to provide access through the door.

One company that currently sells a personal identification unit is affinitex, a division of AiT, and the product name is VeriMe. Because of the size of the fingerprint reader incorporated in the VeriMe product as well as the batteries and control electronics, the unit is relatively large and is intended to be hung around the neck like a pendant. In contrast, a long-standing desire of many in the biometric community is a biometric technology that can be discretely incorporated in a piece of jewelry such as a wristwatch (for example, see Biometrics; Advanced Identity Verification, Julian Ashbourn, Springer, 2000, pp. 63-4).

There are a number of known biometric products and technologies that rely on optical images of various tissue sites to perform a biometric determination. For example, in U.S. Pat. No. 4,537,484, Fowler, et al. describe an apparatus for collecting a fingerprint image using optical techniques. In U.S. Pat. No. 6,175,407, Sartor describes an apparatus for collecting a palm image using optical techniques. In U.S. Pat. No. 5,291,560, Daugman describes a method for collecting and processing an optical image of the iris. In U.S. Pat. No. 5,793,881, Stiver et al. describe a system and method for collecting an image of the subcutaneous structure of the hand using an imaging methodology. However, all of these technologies generate and use images of the tissue as the basis for a biometric determination. The use of imaging generally requires high-quality expensive optical systems and an imaged region that is of sufficient size to capture the necessary biometric detail. If the imaged region is made too small, the biometric performance of these imaging systems degrade. For this reason, contact imaging systems such as fingerprint and palm readers require a relatively large, smooth, accessible surface, limiting the range and form of products in which such systems can be incorporated. Finally, because the determination of a match between enrolled images and the test images is dependent on the orientation of the two images, such biometric systems have to correct for these positional effects. For this reason, biometric systems that rely on imaging techniques require a significant computational power and a sophisticated algorithm to correct for image displacements, rotations and distortions, which leads to increased system cost and increased time required for user authentication.

As an alternative to imaging techniques, the use of spectral information for biometric determinations is disclosed in U.S. patent application Ser. No. 09/832,534, filed Apr. 11, 2001, entitled "Apparatus and Method of Biometric Identification or Verification of Individuals using Optical Spectroscopy", which is a continuation-in-part of U.S. patent application Ser. No. 09/415,594, filed Oct. 8, 1999, entitled "Apparatus and Method for Identification of Individuals by Near-Infrared Spectrum". The equipment used to perform the measurements disclosed in these applications was based on relatively large and expensive multi-purpose laboratory-grade commercial spectrometers. The family of techniques disclosed in these applications is referred to as spectral biometrics. The disclosures of these applications are incorporated herein by reference.

It is well known that tissue spectra are generally affected by both the absorption and scattering properties of the tissue. For many spectral measurement applications the portion of the measured spectra that represent the absorption characteristics of the tissue are more important for the measurement rather than the effects due to scatter. One technique for separating the two effects is known as radially resolved diffuse reflectance spectroscopy, which is based on collecting multiple measurements with different source-detector separation distances. This collection of data provides enough information to estimate and separate effects due to scatter and absorption (see Nichols, et al., *Design and Testing of a White-Light, Steady-State Diffuse Reflectance Spectrometer for Determination of Optical Properties of Highly Scattering Systems*, Applied Optics, Jan. 1, 1997, 36(1), pp 93-104). Although the use of multiple source-detector separations is a well-known technique for analyte measurements in biological samples, the use of similar measurement configurations for spectral biometric determinations has not been previously disclosed.

There is a need for an inexpensive, rugged and small spectrometer to perform spectral biometric determinations. One method that can be used to construct such spectrometers is based on using multiple discrete light sources such as light emitting diodes (LEDs), laser diodes, vertical cavity surface emitting lasers (VCSELs), and narrow band optical filters coupled to a broad-band optical source such as an incandescent bulb or blackbody emitter, operating at different wavelengths to illuminate and measure the optical properties of the sample at each of these wavelengths. These types of spectrometers are known and used for collecting spectrometric information for many applications. For example, in U.S. Pat. No. 3,910,701, Henderson et al. disclose a spectrometer that incorporates a plurality of LED sources for measuring a variety of biological samples. In U.S. Pat. No. 4,857,735, Noller discloses a spectrometer using one or more LEDs to measure solution samples. In U.S. Pat. No. 5,257,086, Fately et al. disclose an optical spectrometer having a multi-LED light source incorporating Hadamard or Fourier frequency encoding methods. However, there is a need for a small, rugged, and inexpensive spectrometer with designs that are optimal for biometric determinations.

As part of the biometric determination task, there is a need for ensuring that the sample being used for the biometric determination is alive. For example, U.S. Pat. No. 5,719,950 to Osten et al. disclose a method and system to combine a biometric-specific measurement such as fingerprints, palm prints, voice prints, etc with a separate measurement of a non-specific biometric parameter such as skin temperature, pulse, electrocardiogram or tissue spectral features to ensure the liveness of the sample.

In addition to performing a biometric identification or verification and ensuring that the sample being measured is living tissue, there may also exist a need to determine an estimate of the age, sex, and other demographic characteristics of the person under test as part of the biometric determination task. For example, the U.S. Federal Trade Commission recently established a commission to examine the issue of remotely determining age of a person who is attempting to access a web site in order to block access by children to inappropriate sites. The Commission on Online Child Protection (COPA) heard testimony on Jun. 9, 2000 that indicated that then-known biometric techniques could not be used to aid the determination of a person's age based on any known biometric features.

BRIEF SUMMARY OF THE INVENTION

Detailed embodiments of the present invention are disclosed herein. However, it is to be understood that the disclosed embodiments are merely exemplary of the present invention, which may be embodied in various systems. Therefore, specific details disclosed herein are not to be interpreted as limiting, but rather as a basis for the claims and as a representative basis for teaching one of skill in the art to variously practice the invention.

The present invention is based on Applicant's recognition that an accurate, precise and repeatable tissue spectra of an individual including selected wavelengths in the near ultraviolet range, visible range, very near infrared range or near infrared range and combinations of selected wavelengths from these ranges contains spectral features and combinations of spectral features which are unique to that individual. The spectral range over which biometric determinations have been demonstrated span wavelengths from 350 nm to 2500 nm, although it is likely that similar capabilities exist outside of this range. The choice of which measurement wavelengths to use is driven in part by the availability and cost of suitable illumination sources and detectors. In the case of the discrete light sources disclosed in this application, the most common and least expensive optical components work with light in the wavelength region from 350-1000 nm. Such a system can be constructed from silicon detector material and readily available LEDs, laser diodes, VCSELs, or optical filters coupled to a bulb. However, other detectors and other light sources could also be used as alternative components or to span a greater spectral range or a different spectral range.

The present method and apparatus also provides for biometric determination of whether a sample being measured is living tissue, known as a "liveness" determination. Further, the present system maintains high system security because the biometric device ensures that the exact sample it is operating on is real and alive, in addition to matching the properties of the enrolled data. Thus, an accurate determination of liveness precludes the use of simulated body parts and/or parts that have been removed from authenticated individuals. It has been found that the spectroscopic signature of living tissue is substantially different than most other media (including dead tissue), and thus liveness determination is an integral part of the present biometric device and method.

The present method and apparatus can also be used to estimate or verify the age of a person undergoing the biometric measurement. Further, the present method and apparatus can be used to estimate or verify the sex of the person undergoing the biometric measurement.

A variety of embodiments are disclosed herein for a sensor apparatus that can obtain tissue spectra that can be utilized for biometric identification determinations, liveness determinations, age determinations and sex determinations. These embodiments of the present invention are amenable to miniaturization and ruggedization for incorporation in a variety of systems. Such fixed-installation applications include, but are not limited to, physical entry assurance to workplaces, homes, hotels, secure industrial areas and other controlled sites; time and attendance monitoring; automotive applications such as keyless entry, keyless start, automotive personality setting, and mobile internet access; personal computer and network security; secure health record access; automated financial transactions; and authorized handgun use.

In addition to the fixed-system applications, the apparatus and methods disclosed in this application can be used in small personal biometric packages such as smart cards, electronic fobs or wristwatches that the user/owner/wearer can carry with them and provide biometrically-assured authorization to a variety of devices and systems. Such personal biometric systems act as keys that provide access to protected property only if activated by the authorized individual, and reduces or eliminates entry to the protected system by unauthorized people. Thus, the personal biometric devices of the present invention become a type of smart key that allow access to any system that interfaces to such device and for which the holder is authorized to access. Such systems and uses can include, but are not limited to, personal computers, network access devices, doors in office buildings and private residences, time-and-attendance systems, automobiles, security equipment, automated financial transactions, cellular telephones, toll booths, electronic vending machine transactions and pay-per-entry events such as movies, etc.

Alternatively, as personal electronics such as personal digital assistants (PDA) and cellular phones become integrated in a variety of wireless applications, the present invention provides a means to confirm the identity of the person using the device. This can be important when wireless applications such as mobile commerce use such devices to authorize monetary transfers or make purchases, while also allowing access to medical records and act as an electronic key for homes, offices and automobiles. By providing an integrated, compact, rugged, secure biometric system that can be used to confirm the identity of a person attempting to use the PDA to access protected property, the present invention provides a capability that is applicable in many everyday life situations.

In addition to the application of the spectral biometric sensor as a single biometric, the sensor and identification methods disclosed in this application can also be used in conjunction with other biometric techniques within a system to either increase the accuracy of the system or increase the robustness of the system. In cases where greater system security is required, the spectral biometric technique may be combined with one or more other biometric methods and the results can be combined to ensure a person's identity. Alternatively, the disclosed systems and methods can be combined with other biometric techniques to offer more than one method to identify a person in case one method is disabled due to system failure or other reason, ensuring a more robust system performance overall.

One system for performing biometric determinations includes: an optical sensor head consisting of one or more monochromatic illumination sources, one or more detectors, and an optical sampler, all arranged such that there exists a plurality of source-detector spacings or a plurality of different monochromatic wavelengths, or both; a light-source encoding system; a microprocessor with an input and output device; a database including selected tissue spectral data for authorized persons or a collection of spectral data for individuals against which unknown individual's would be checked; and a program running in the microprocessor for discriminating between a target individual's spectral data and the authorized spectral data or collection of spectra database containing spectra for a group of individuals. The program can include software for performing an analysis for liveness determination, age determination, and sex determination based on the measured spectral data.

These and various other advantages and features of novelty which characterize the present invention are pointed out with particularity in the claims annexed hereto and forming a part hereof. However, for a better understanding of the invention, its advantages, and the object obtained by its use, reference should be made to the drawings which form a further part hereof, and to the accompanying descriptive matter in which there are illustrated and described preferred embodiments of the present invention.

BRIEF DESCRIPTION OF THE DRAWINGS

In the drawings, in which like reference numerals indicate corresponding parts or elements of preferred embodiments of the present invention throughout the several views.

DETAILED DESCRIPTION OF THE INVENTION

Figure 1:
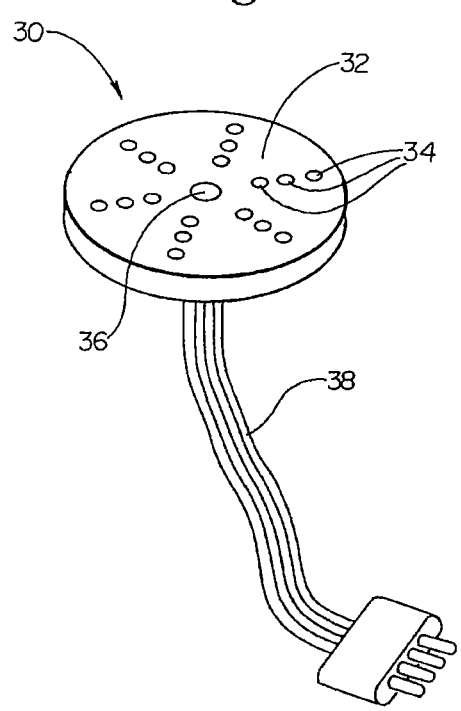
FIG. 1 is a perspective view of a spectral biometric sensor head in one preferred embodiment.

Detailed embodiments of the present invention are disclosed herein. However, it is to be understood that the disclosed embodiments are merely exemplary of the present invention which may be embodied in various systems. Therefore, specific details disclosed herein are not to be interpreted as limiting, but rather as a basis for the claims and as a representative basis for teaching one of skill in the art to variously practice the invention.

The present invention is based on Applicant's recognition that an accurate, precise and repeatable tissue spectrum of an individual in the near ultraviolet range, visible range, very near infrared, or near infrared spectral range and combinations of these ranges contains spectral features and combinations of spectral features which are unique to that individual. The present invention is further based on a recognition that proper analysis, utilizing discriminant analysis techniques, can identify these unique features or combinations, which are not readily apparent in visual analysis of a spectral output, so that an individual's identity may be determined by comparison of tissue spectral data taken at the time of use and compared to stored tissue spectral data from prior measurement.

In addition, the tissue spectrum has been found to not only contain information that is unique to an individual, but also contains numerous features and combinations of features that indicate whether such spectral samples were taken while the sample was alive or not. The physiological effects that give rise to spectral features that indicate the state of a sample (alive or dead) include but are not limited to blood perfusion, temperature, hydration status, glucose and other analyte levels, and overall state of tissue decay. Thus, the biometric identification and verification methods of the present invention can be also used in conjunction with, or separately from, the determination of the state of the liveness of the tissue. Tissue from other biological systems (organs, animals, etc.) has also been found to have spectral characteristics that are distinctly different from human skin due to differences in the tissue composition and form. Thus, the biometric identification methods of the present invention can be also used in conjunction with or separately from the determination of whether the sample is human skin or some other tissue. In addition, it has been found that tissue-like substances such as collagen gelatin, latex, water solutions, or others have spectral characteristics that are distinctly different than human tissue due to differences in composition and form. The biometric identification and verification methods of the present invention can thus be used with or separately from the determination whether the sample is actual tissue or some other substance.

While utilizing the present invention, it has also been found that other spectral features observed in the tissue spectrum relate to the age and sex of the person being measured. It is believed that these features are due in part to the differences in dermal thickness between young and old people and between males and females. Such changes in skin thickness and composition affect the optical characteristics of the tissue by affecting the scattering properties of the sample. These properties in turn impose distinct spectral shapes on the measured tissue spectra, which can be extracted and used by appropriate multivariate techniques to provide age and sex estimates.

Referring now to FIG. 1, a perspective view of an embodiment of a typical optical sensor head of the present invention is shown. The sensor assembly 30 consists of a series or plurality of light sources 34 arranged in a selected manner on a sensor head 32, which also contains one or more detectors 36. The sensor assembly 30 may also include power conditioning electronics (not shown), which supply power to the light sources 34 and may also include signal processing electronics (not shown) which amplify the resulting signal from the detector 36. A multi-conductor cable 38 provides a means to power the sensor head and to transmit the detected signal back to the microprocessor or computer (not shown) that processes the spectral data.

The light sources 34 can be light emitting diodes (LEDs), laser diodes, vertical cavity surface emitting lasers (VCSELS), quartz tungsten halogen incandescent bulbs with optical pass-band filters with optical shutters, or a variety of other optical sources known in the art. The light sources 34 can each have the same wavelength characteristics or can be comprised of sources with different center wavelengths in the spectral range from about 350 nm to about 2500 nm. In general, the collection of light sources 34 can include some sources that have the same wavelengths as others and some sources that are different. In a preferred embodiment, the light sources 34 includes sets of LEDs, laser diodes, VCSELs, or other solid-state optoelectronic devices with differing wavelength characteristics that lie within the spectral range from about 350 nm to about 1100 nm.

The detector 36 can be a single element or it can be a one- or two-dimensional array of elements. The detector type and material is chosen to be appropriate to the source wavelengths and the measurement signal and timing requirements. These detectors can include PbS, PbSe, InSb, InGaAs, MCT, bolometers and micro-bolometer arrays. In a preferred embodiment where the light sources 34 are solid-state optoelectronic devices operating in the spectral range from about 350 nm to about 1100 nm, the preferred detector material is silicon.

The light sources 34 can be sequentially illuminated and extinguished to measure the tissue properties for each source by turning power to each of them on and off. Alternatively, multiple light sources 34 can be electronically modulated using encoding methods that are known to one knowledgeable in the art. These encoding patterns include Fourier intensity modulation, Hadamard modulation, random modulation, and other modulation methods.

Figure 2:
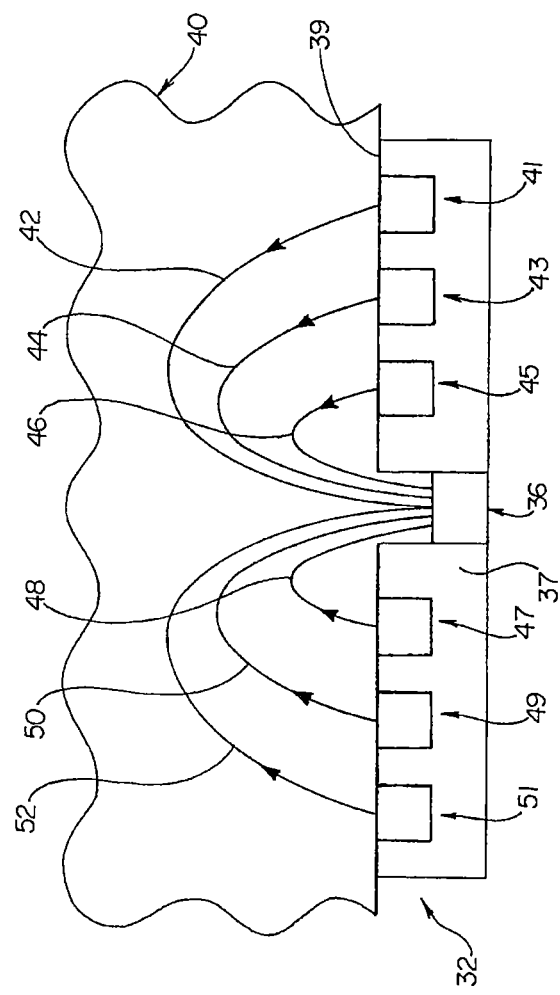
FIG. 2 is a schematic cross-sectional view of the biometric sensor element coupled to the skin surface showing multiple mean optical paths.

FIG. 2 shows a cross-sectional view of the sensor head 32 of FIG. 1, for use in diffuse reflectance measurements. Also shown is the tissue 40 in contact with the face 39 of the sensor head 32 and the mean optical paths 42, 44, 46, 48, 50, 52 of the light traveling from each light source 41, 43, 45, 47, 49, 51, respectively, to the detector 36. In acquiring tissue spectral data, measurements can be made in at least two different sampling modes. The optical geometry illustrated in FIG. 2 is known as diffuse reflectance sampling geometry where the light sources and detector lie on the same side of the tissue. An alternative method is known as transmission sampling, wherein light enters a thin tissue region such as an earlobe or a fingertip on one side and then is detected by a detector located on the other side of the tissue. Although light in such regions as the silicon-region can penetrate tissue to significant depths of one centimeter or more, depending upon the wavelength, transmission sampling of the tissue limits the region of the body that can be used. Thus, while either mode of sampling is applicable to the present invention, and especially to analysis utilizing light in the silicon-region, a preferred and more versatile sampling method is based upon reflected light.

Referring to FIG. 2, when the tissue is illuminated by a particular light source 41, the resulting signal detected by detector 36 contains information about the tissue optical properties along a path between the source 41 and detector 36. The actual path of any given photon is highly erratic due to effects of optical scattering by the tissue, but the mean optical path 42 is a more regular and smooth curve, as shown in the figure.

This mean optical path is, in general, different for different source-detector separation distances. If another light source 51 is located at the same distance from the detector 36 as light source 41 and the two light sources have the same wavelength characteristics, the resulting signals can be combined to increase the resulting signal-to-noise ratio of the measurement. If light source 51 has a different wavelength characteristic than light source 41 then, in general, the resulting signals provide unique and useful information about the tissue optical properties, especially as they relate to spectral biometric determinations and should be analyzed as distinct data points. In a similar manner, if two light sources have the same wavelength characteristics and are positioned at different distances from the detector 36 (for example light sources 41 and 43) then the resulting information in the two signals is different and the measurements should be recorded and analyzed as distinct data points. Differences in both wavelength characteristics and source-detector separation provide new and useful information about the optical characteristics of the tissue 40.

In general, the detector 36 can be located in the center of the sensor head or it can be offset to one side of the sensor head 32 in order to provide for greater source-detector separation distances. The sensor head 32 can be other shapes including oval, square and rectangular. The sensor head 32 can also have a compound curvature on the optical surface to match the profile of the device in which it is mounted.

Light that reflects from the topmost layer of skin does not contain significant information about the deeper tissue properties. In fact, reflections from the top surface of tissue (known as "specular" or "shunted" light) are detrimental to most optical measurements. For this reason, FIG. 2 illustrates a sensor-head geometry wherein the detector 36 is recessed from the sensor surface 39 in optically opaque material 37 that makes up the body of the sensor head 32. The recessed placement of detector 36 minimizes the amount of light that can be detected after reflecting off the first (epidermal) surface of the tissue. It can be seen that the same optical blocking effect could be produced by recessing each of the light sources, or by recessing both the detector and the light sources. Other equivalent means of optical blocking can be readily established by one of ordinary skill in the art.

Figure 3:
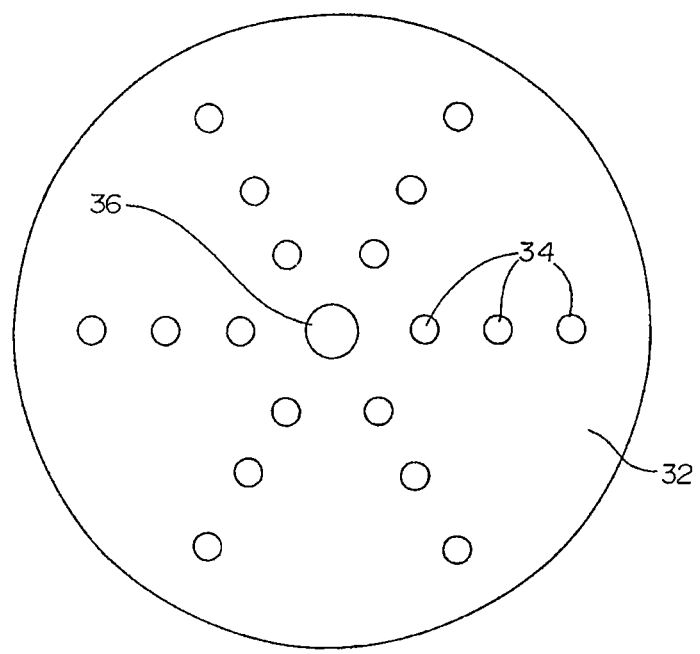
FIG. 3 is a schematic top view of the biometric sensor incorporating multiple light sources arranged with variable source-detector distances.

FIG. 3 shows a top view of the sensor head 32 with plurality light sources 34 and a single detector 36 visible. This figure is intended to be representative of configurations that allows for a variety of sources 34 and detectors 36 that have variable spacing between them. In general, this configuration is most applicable in cases where a small number of light sources 34 with different wavelength characteristics are available. In these cases, the variable distance between sources 34 and detector 36 are used to gather additional optical information from the tissue.

Figure 4:
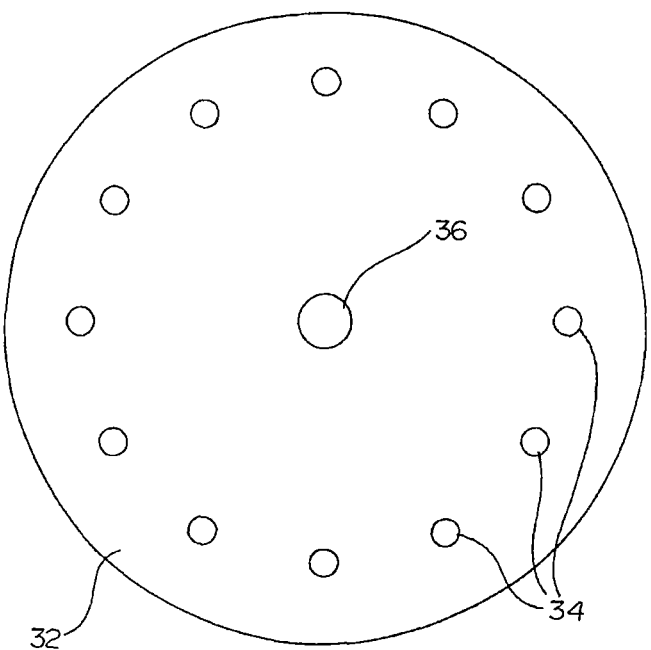
FIG. 4 is a schematic representation of the top view of an alternative biometric sensor incorporating multiple light sources arranged with a common source-detector distance.

Referring to FIG. 4, the light sources 34 can also be arranged to be equidistant from the detector 36. This configuration is most appropriate in cases where each light source 34 is a different wavelength and sufficient light sources can be obtained to achieve the desired accuracy results for the system. An example of this occurs when the individual light sources are the result of combining optical filters with one or more broadband (e.g., incandescent) light sources. In this case, many unique wavelength bands can be defined and each of the sources 34 can be placed equidistant from the central detector 36.

Figure 5:
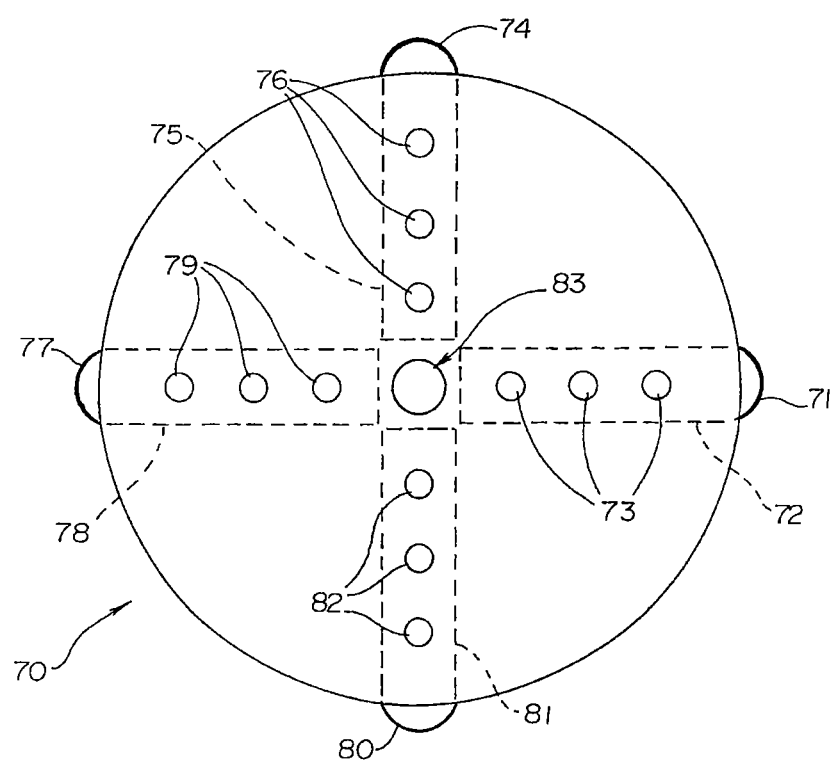
FIG. 5 is a schematic top view of an alternative biometric sensor incorporating multiple light sources and a waveguide/aperture plate to provide variable source-detector distances.

An alternative embodiment of a variable source-detector configuration is illustrated in FIG. 5, which schematically depicts a top view of a sensor 70 of this type. In this embodiment, the four different light sources 71, 74, 77, 80 are arranged around a common detector 83. Four different light sources 71, 74, 77, 80 are shown for illustration but fewer or more can be used in a particular embodiment. Each of the light sources 71, 74, 77, 80 is optically coupled to a different optical waveguide 72, 75, 78, 81. Each waveguide 72, 75, 78, 81 has individually controllable electronic or mechanical optical shutters 73, 76, 79, 82. These optical shutters 73, 76, 79, 81 can be individually controlled to encode the light by allowing light to enter the tissue from a waveguide 72, 75, 78, 81 at a predetermined position or positions. One method for implementing optical shutters is using micro-electromechanical systems (MEMS) structures, which is a technology well known to one of ordinary skill in the art. The light sources 71, 74, 77, 80 can be different LEDs, laser diodes or VCSELs. Alternatively, one or more incandescent sources with different optical filters can be used to generate light of different wavelength characteristics to couple into each of the waveguides 72, 75, 78, 81. As well, this MEMS aperture geometry could be used with other illumination sources and geometries illustrated in the other figures in this application.

Figure 6:
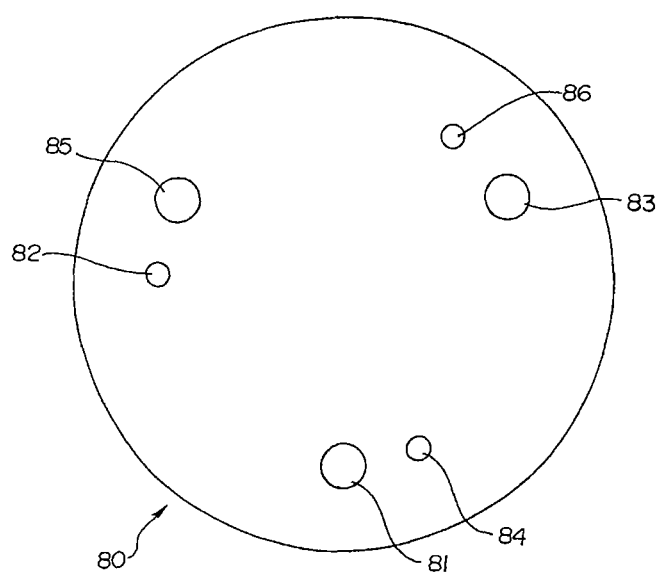
FIG. 6 is a schematic top view of an alternative biometric sensor including multiple light sources and multiple detectors providing variable source-detector separations.

Alternatively, multiple source-detector distances can also be achieved by using more than one detector element as shown in FIG. 6. FIG. 6 schematically depicts a top view of a sensor 80 of this type. In this embodiment, each of three different light sources 82, 84, 86 is positioned relative to three detectors 81, 83, 85 such that the spacing between a given light source and each of the detectors is different. For example, the source detector spacing for a light source 82 is shortest with respect to detector 85 and longest with respect to detector 83. By turning on the light sources 82, 84, 86 in a sequential or encoded pattern and measuring the response at each of the three detectors 81, 83, 85, the tissue characteristics for all of the available source-detector separations at all of the wavelengths can be measured.

Figure 7:
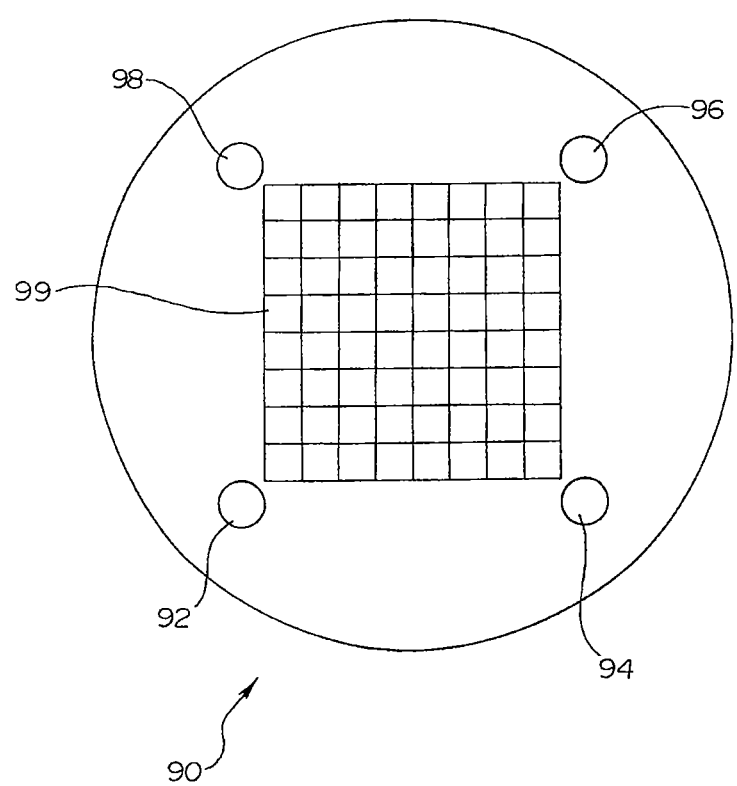
FIG. 7 is a schematic top view of an alternative biometric sensor incorporating multiple light sources and a detector array for providing variable source-detector separations.

The use of multiple detector elements and multiple illumination sources can be extended to using a detector array as shown in FIG. 7. FIG. 7 schematically depicts a top view of a sensor 90 of this type. In this embodiment, multiple light sources 92, 94, 96, 98 are placed at the perimeter of a detector array 99. The signal detected at each of the array elements then represents a different source-detector separation with respect to the light from a given light source. Many variants on this configuration exist including the use of one-dimensional (1-D) or two-dimensional (2-D) arrays, and placing sources within the array as well as on the periphery.

The detector(s) can be any material appropriate to the spectral region being detected. For light in the region from about 350 nm to about 1100 nm, a preferred detector material is silicon and can be implemented as a single-element device, a collection of discrete elements, or a 1-D or 2-D array, depending upon the system configuration and encoding method used. For light in the region from about 1.25 to about 2.5 .mu.m, a preferred detector material is InGaAs and can also be implemented as a single element, a collection of elements, or a 1-D or 2-D array. Additional detector materials and means of detection include InSb, Ge, MCT, PbS, PbSe, bolometers, and others known to one of ordinary skill in the art.

Once the light passing though the tissue is detected, the signals can be digitized and recorded by standard techniques. The recorded data can then be processed directly or converted into absorbance spectra or noised-scaled absorbance spectra as is known to one of ordinary skill in the art. The data can then be used for spectral identification or verification by the methods described in U.S. patent application Ser. No. 09/832,534, filed Apr. 11, 2001, entitled "Apparatus and Method of Biometric Identification or Verification of Individuals using Optical Spectroscopy", and U.S. patent application Ser. No. 09/415,594, filed Oct. 8, 1999, entitled "Apparatus and Method for Identification of Individuals by Near-Infrared Spectrum".

A small spectral biometric subassembly, such as those discussed above, can be embedded in a variety of systems and applications. The spectral biometric reader can be configured as a dedicated system that is connected to a PC or a network interface, an ATM, securing an entryway, or allowing access to a particular piece of electronics such as a cellular phone. In this mode, one or more people can be enrolled in the biometric system and use a particular reader to gain access to a particular function or area.

Alternatively, the spectral biometric system can configured as a personal biometric system that confirms the identity of the sole person authorized to use the device, and transmits this authorization to any properly equipped PC, ATM, entryway, or piece of electronics that requires access authorization. One advantage of this latter approach is that the personal biometric system can transmit an identifying code to the requesting unit and then use the biometric signal to confirm authorization, which implies that the system needs to perform a verification task rather than the more difficult identification task. Yet, from the user's perspective, the system recognizes the user without an explicit need to identify himself or herself. Thus, the system appears to operate in an identification mode, which is more convenient for the user.

An additional advantage of a personal biometric system is that if an unauthorized person is able to defeat the personal biometric system code for a particular biometric system-person combination, the personal biometric system can be reset or replaced to use a new identifying code and thus re-establish a secure biometric for the authorized person. This capability is in contrast to multi-person biometric systems that base their authorization solely on a biometric signature (spectral, as well as any of the other biometric techniques such as fingerprint, iris, facial, etc.). In this latter case, if an intruder is able to compromise the system by somehow imitating the signal from an authorized user, there is no capability to change the biometric code since it is based solely on a fixed physiological characteristic of a person.

Figure 8:
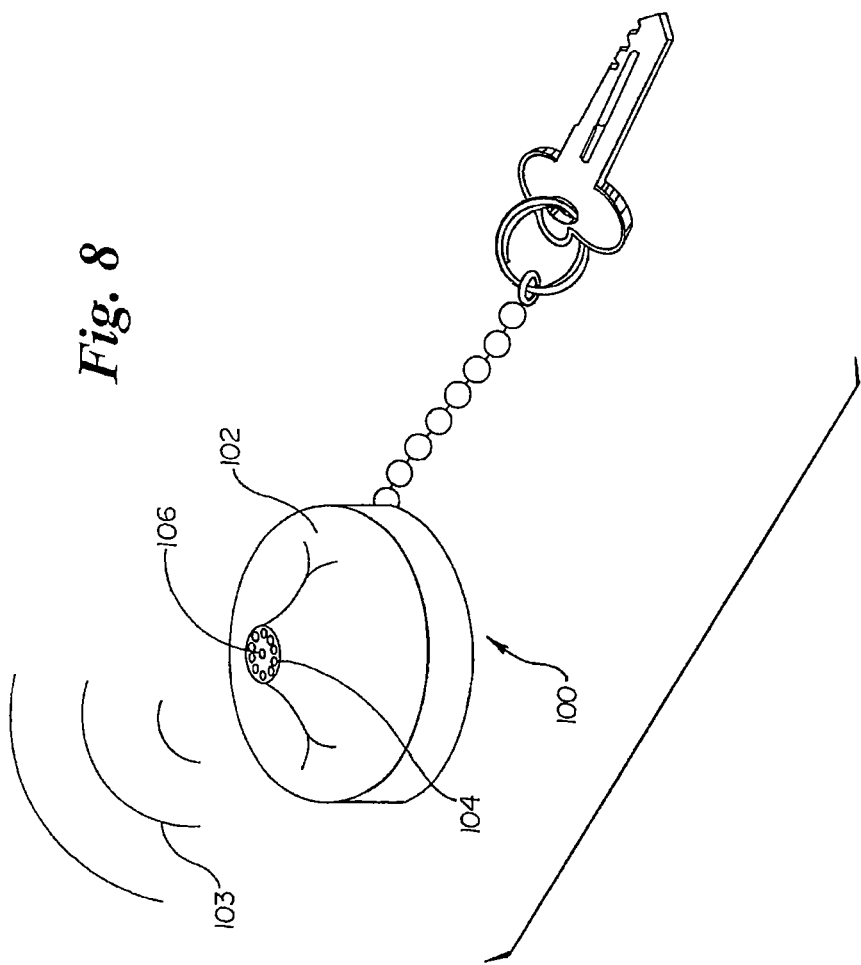
FIG. 8 is a schematic representation of a personal biometric sensor built into a key fob.

FIG. 8 shows one embodiment of a personal spectral biometric system 100 in the configuration of an electronic key fob 102. The equidistant sensor configuration of FIG. 4 is shown for illustration purposes only. Any of the disclosed sensor configurations are application in the electronic key fob. The illumination 104 and detection system 106 are built into the fob 102, as is the means to collect and digitize the spectral information. In one embodiment, short-range wireless techniques based upon RF signals 103 can be transmitted to communicate between the fob and a corresponding reader (not shown) that allows access to the PC, entryway, etc. In another embodiment, an infrared optical signal can be used to transmit the information between the fob and the reader. In another embodiment, a direct electrical connection is established between the personal biometric system and the reader. The actual comparison between the measured spectral data and the previously recorded enrollment spectrum (template) can be made either within the fob or at the reader. In the former case, the logical operations necessary to perform the comparison are done within the fob and then a simple confirmed or denied signal is transmitted to the reader. In the latter case, the most recent measured spectrum is transmitted to the reader and the comparison and decision is accomplished at the reader or at a host to which the reader is connected. In either case, the communication between the fob and the reader needs to be performed in a secure manner to avoid interception and unauthorized use of the system. Methods for ensuring secure communication between two devices are well known to one of ordinary skill in the art.

Figure 9:
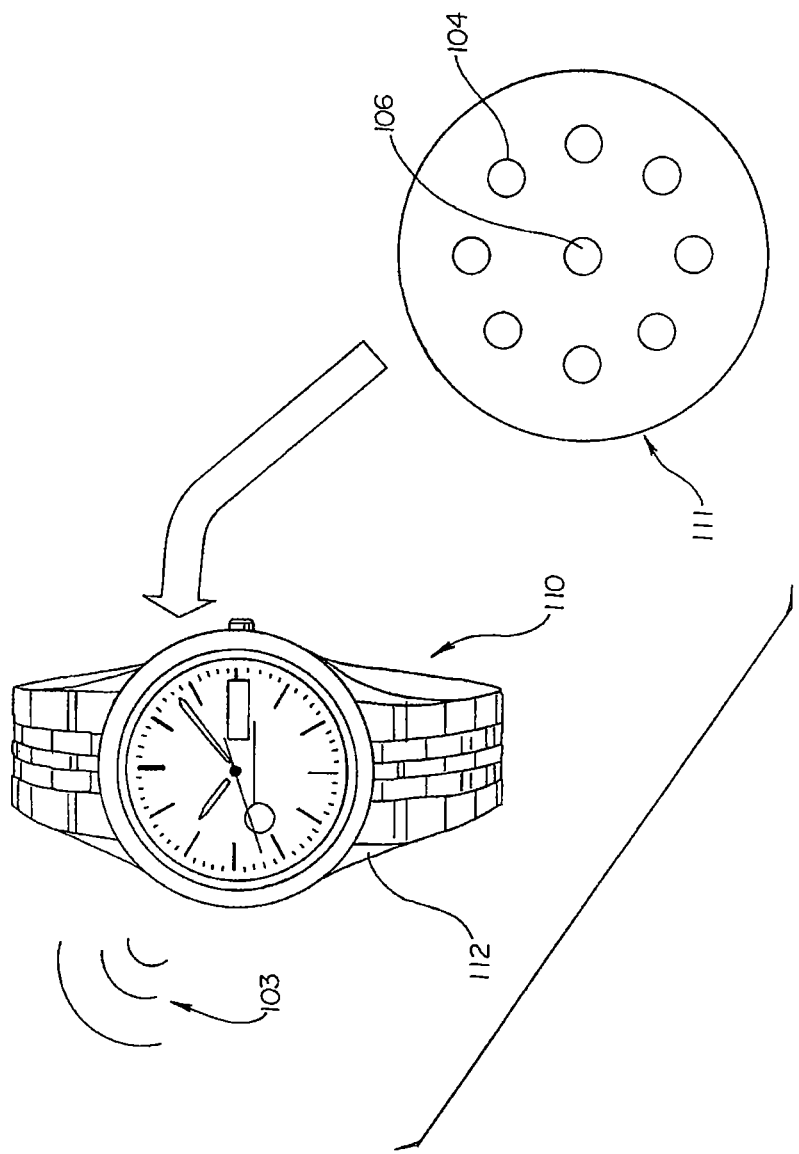
FIG. 9 is a schematic representation of a watch including a personal biometric sensor built into a back faceplate of the watch.
Figure 10:
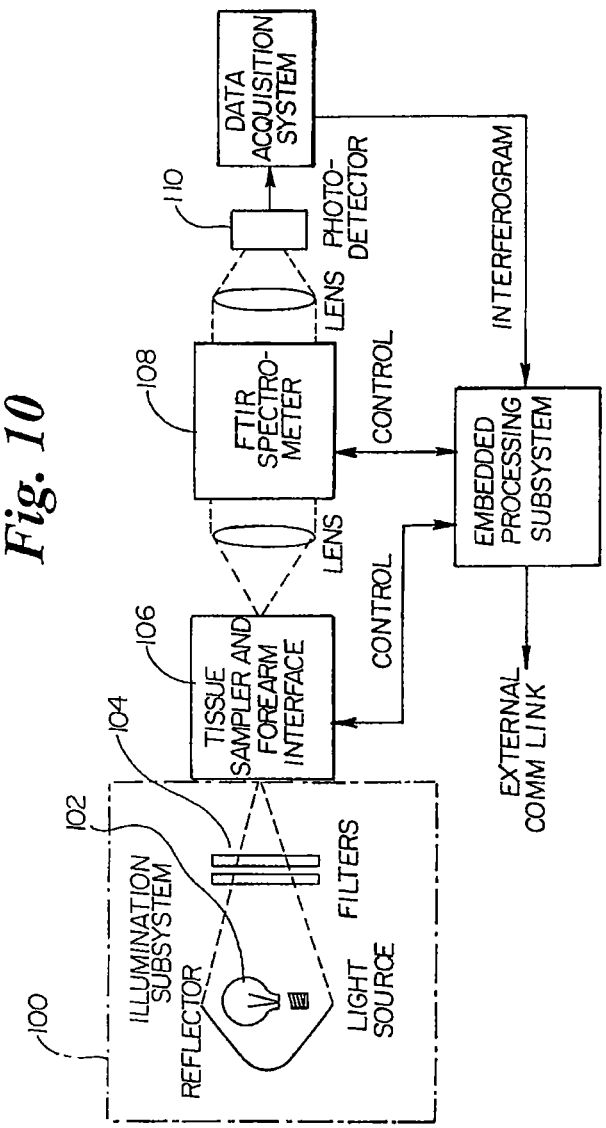
FIG. 10 is a schematic of a laboratory spectrometer system that was used to perform experiments to confirm performance of spectral biometric devices.

A second embodiment of a personal spectral biometric system 110 is depicted in FIG. 9. In this case, the biometric reader 111 is built into the case of a watch 112 and operates based upon signals detected from the skin in the area of the wrist. The operation of this system is identical to the operation described for the biometric fob. FIG. 10 shows the equidistant-sensor geometry of FIG. 4 for illustration purposes only. Any of the sensor geometries previously disclosed can be used in this application.

In addition to the watch or fob, similar biometric capability can be built into other personal electronic devices. These devices include personal digital assistants (PDAs) and cellular telephones. In each case, the personal biometric system can provide user authorization to access both the device in which it is installed, as well as to provide authorization for mobile commerce (M-Commerce) or other wireless transactions that the device is capable of performing.

The compact sensors disclosed can also be put into firearms to prevent unauthorized usage. In particular, the biometric sensor could be placed in the handgrip of a weapon such as a handgun or other firearm to sense tissue properties while the gun is being held in a normal manner. A further capability of the apparatuses and methods disclosed in this application is the ability to identify people who are to be explicitly excluded from accessing protected property as well as determining those who are authorized to access the property. This capability will improve the biometric performance of the system with respect to those unauthorized people who are known to attempt to use the device, which could be particularly important in the case of a personal handgun. In particular, parents who own a biometrically enabled handgun can enroll themselves as authorized users and also can enroll their children as explicitly unauthorized users. In this way, parents could have further insurance that children who are known to be in the same household as a gun will not be able to use it.

It is also possible to use the explicit-denial capability of a biometric system in a fixed installation such as a home, place of business, or an automobile. For example, a biometric system installed at the entryway of a place of business can be used to admit authorized employees and temporary workers. If an employee is fired or the term of the temporary employee expires, then their enrollment data can be shifted from the authorized to the unauthorized database, and an explicit check is made to deny access to the former employee if he or she attempts to enter.

Because of the nature of optical spectroscopy, it is difficult to generate spectra of similar shape and absorbance characteristics without using similar material for the sample. For this reason, many common materials, such as latex and wax that are used to defeat other biometric systems such as fingerprint readers or hand geometry systems are ineffective tissue surrogates for a spectral biometric system. By performing a spectral comparison, most non-tissue samples will be rejected, resulting in a strong countermeasure capability against potential intruders.

Similarly, many of the spectral features that are present in the wavelength ranges disclosed by this invention are indicative of living tissue. These features include oxy- and deoxy-hemoglobin bands, temperature effects, intracellular hydration, and others. These effects contribute to the overall spectral signature of the sample being measured and ensure that a matching sample is one that is part of a living person and normally perfused. Thus, a good spectral comparison ensures the "liveness" of a sample and deters the use of dead or excised tissue as a means to circumvent the spectral biometric system.

In some applications, such as Internet access authorization, it may be useful to be able to verify the sex and/or age of the person using the spectral biometric system. Because of both age- and sex-specific difference in skin structure and composition, the optical spectra change in systematic and indicative ways such that the age and sex can be estimated using the biometric spectral data.

In practicing the present invention, the tissue spectral data is determined by measuring the light intensity received by the output sensor for the various light sources which give indications of the optical properties of the tissue at different wavelengths and/or at different source-detector separations. As is well known to one of ordinary skill in the art, the signal produced by the detector in response to the incident light levels can be converted into spectral data that can be recorded and used for subsequent analysis for enrollment or authorization of identity.

Experimental Results

A laboratory experiment was performed to test and confirm the premise that discrete wavelength light sources could be used for biometric determination tasks and that further advantage could be gained by arranging the same sources with different source-detector spacings. FIG. 10 shows a schematic of the laboratory system that was used in this experiment. This system used an illumination subsystem 100 that incorporated a 100 W quartz tungsten halogen bulb 102 and some optical filters 104 to transmit light in the 1.25 to 2.5 .mu.m spectral range. The light was directed into a fiber-optic optical sampler 106, which was used to take diffuse reflectance optical measurements of the volar surface of the forearm. Diffusely reflected light collected by the sampler 106 was then directed into a Fourier transform infrared (FTIR) spectrometer 108 and detected by an extended range indium gallium arsenide (InGaAs) detector 110. The spectrometer was a Perkin Elmer 2000 FTIR operating with a spectral resolution of 16 cm.sup.−1. The resulting interferogram data were digitized, stored and converted to spectral data using techniques well known to one of ordinary skill in the art.

Figure 11:
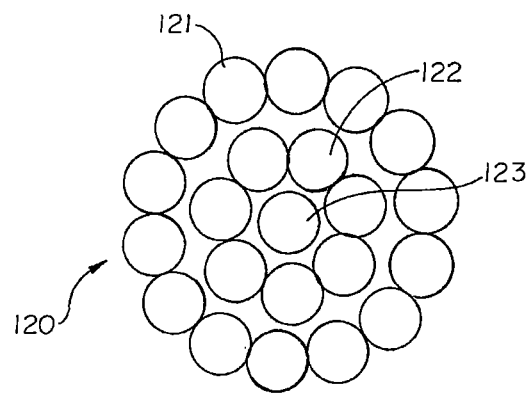
FIG. 11 is a schematic diagram of an end view of a dual-path fiber optic sampler.

The optical sampler 106 included a sample head 120 which was capable of collecting tissue spectral data using two different source-detector spacings. FIG. 11 shows a top view of the optical sampler or sample head 120 including three different optical fiber groupings: an outer ring 121, an inner ring 122 and a central bundle 123. The outer ring of optical fibers 121 and inner ring of optical fibers 122 were used to illuminate the tissue and the central bundle of fibers 123 was used to collect the diffusely reflected light. An optical switch (not shown) was built into the optical sampler subsystem such that either the outer ring of optical fibers 121 or the inner ring of optical fibers 122 was illuminating the tissue at any one time. The center-to-center spacing of the inner ring fibers 122 to the center detection bundle 123 was approximately 0.5 mm while the outer ring 121 separation was approximately 0.7 mm. Thus, spectra collected when the outer ring was illuminating the tissue had a longer and deeper average path length than spectra collected with inner ring 122 illumination. The optical system was set up so spectra were collected alternately using inner and outer illumination closely spaced in time.

Twenty-two diabetic subjects participated in a study, which spanned a total duration of 16 weeks. Each person in the study was measured during two separate visits per week for each of the first 7 weeks of the study. There was then an 8-week gap, followed by one additional week of study where each person again was measured during two separate visits. During each measurement visit, multiple (5) optical samples were collected from the underside of their left forearm. Each optical sample consisted of 90 seconds of measurement time.

The optical samples collected by the sampler shown in FIG. 11 were used to simulate a discrete source configuration similar to that shown in FIG. 3. Although the system shown in FIG. 11 is a broadband illumination system, the spectral data collected on this laboratory system were post-processed to emulate a discrete wavelength system. A small number of uniformly spaced, discrete spectral elements (variously 4, 6, 10, or 20) were selected from the continuous spectral data and used for subsequent biometric analysis using the same type of analysis described previously. The biometric determinations were made in a manner very similar to the technique described in U.S. patent application Ser. No. 09/832,534, filed Apr. 11, 2001, entitled "Apparatus and Method of Biometric Identification or Verification of Individuals using Optical Spectroscopy". In particular, the biometric analysis was performed by randomly selecting a small number of subjects' data as from authorized users ("validation"), a different small subset as non-authorized users ("intruders"), and the remaining subjects' data were used to build a calibration set. Due to the relatively small number of subjects, the analysis used six random subjects for validation and two as intruders. This analysis was repeated 10 times and output was pooled to achieve stable results.

The calibration data were processed to produce generic data as described in U.S. Pat. No. 6,157,041, entitled "Methods and Apparatus for Tailoring Spectroscopic Calibration Models". A PCA decomposition of these data was performed to generate 50 eigenvectors and scores. The scores were then analyzed to determine the 20 factors that had the largest values for the ratio of the between-person variation to the within-person variation for each set of scores.

The first two samples for each of the validation subject's data were averaged and used as the initial enrollment spectra. Each of the remaining validation spectra were taken in temporal sequence and subtracted from the enrollment spectrum. This spectral difference was then presented to the selected calibration factors and a Mahalanobis distance was calculated. If the Mahalanobis distance was below a certain threshold value, the validation spectrum was deemed valid, and a weighted sum of the validation spectrum (0.2) and the enrollment spectrum (0.8) was used to update the enrollment spectrum. This process was repeated for multiple threshold values. One of ordinary skill in the art will recognize that the Spectral F-Ratio could be used instead of or in conjunction with the Mahalanobis distance metric to perform the identity determinations. The intruder data was processed in a similar manner as the validation data using the same threshold values.

This analysis was applied to spectral data from inner ring illumination, from outer-ring illumination, and to a data set that concatenated the selected data from both inner- and outer-ring illumination. This latter case simulated the condition where one pair of some number, N, of different discrete sources were used for illumination at two different source-detector distances and data were collected for each of the 2N sources separately.

Figure 12:
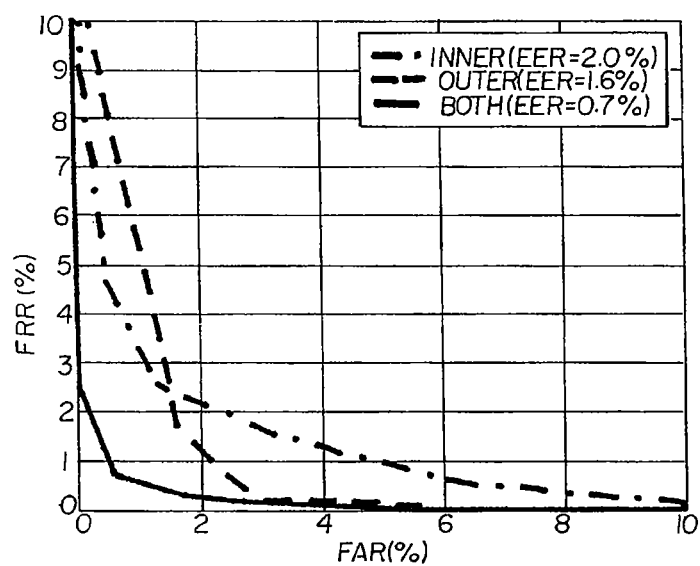
FIG. 12 is a graph depicting receiver-operator characteristics for the dual-path sampler of FIG. 11.
Figure 13:
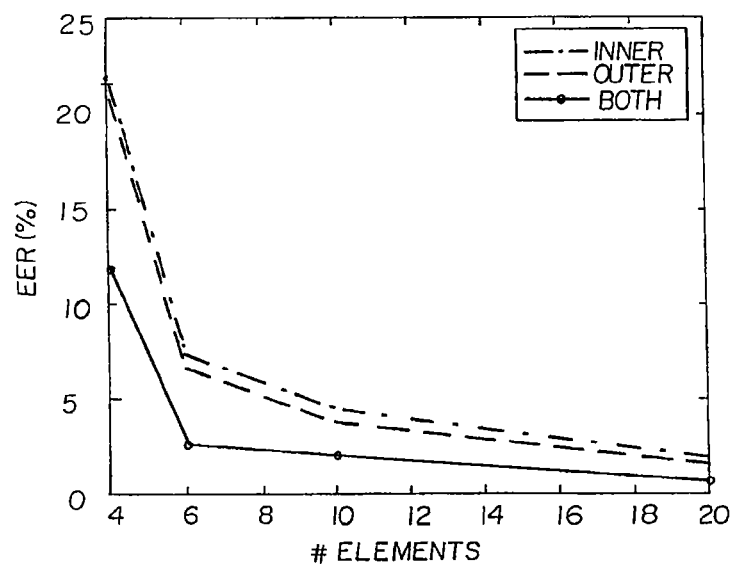
FIG. 13 is a graph depicting equal error rates for the dual-path sampler analysis using variable numbers of discrete spectral elements.

The results of this analysis are shown in FIGS. 12 and 13. FIG. 12 depicts the receiver-operator characteristic (ROC) curves for the case where 20 of the spectral elements were used for biometric identification tasks. The equal error rate (EER, defined as the false acceptance rate=false rejection rate) of the inner-ring data is 2.0% while the outer-ring data yields an EER of 1.6%. In contrast, a spectral data set made up of both of the inner- and outer-ring spectral elements gives an improved EER of 0.7%. FIG. 13 shows the EER for all three sampling conditions for cases where 4, 6, 10, and 20 elements are used for analysis. In all cases, the combined-ring data performs much better than either of the separate channels, indicating that additional biometric information is available by using the same wavelengths to measure tissue with multiple source-detector separations.

The ability to assess age using spectral data was tested using the NIR spectra from a multi-person study that was conducted using a laboratory-grade FTIR system similar to that shown in FIGS. 10 and 11. However, the light source 102 was a 40 W quartz tungsten halogen bulb, the FTIR spectrometer 108 was a Bomem WorkIR, and the optical sampler 106 consisted of a just a single illumination ring and a central detector fiber bundle similar to the inner ring 122 and central bundle 123 shown in FIG. 11.

The data were collected from 87 diabetic people who participated in a portion of a 17-week study. Approximately half of the people participated in the study for 6 weeks and half participated for 11 weeks. In either case, each person was measured during two separate visits per week for each week they participated in the study. During each measurement visit, multiple (3-5) optical samples were collected from the underside of their left forearm. Each optical sample consisted of 90 seconds of measurement time. A total of more than 5100 optical samples were collected on this study group. The resulting intensity spectra were log-transformed to pseudo-absorbance data and a scale function was applied to the spectra to make the spectral noise characteristics uniform. Standard outlier metrics (Mahalanobis Distance and Spectral F-Ratio) were applied to the resulting scaled absorbance data to remove outlying spectra before subsequent processing.

Figure 14:
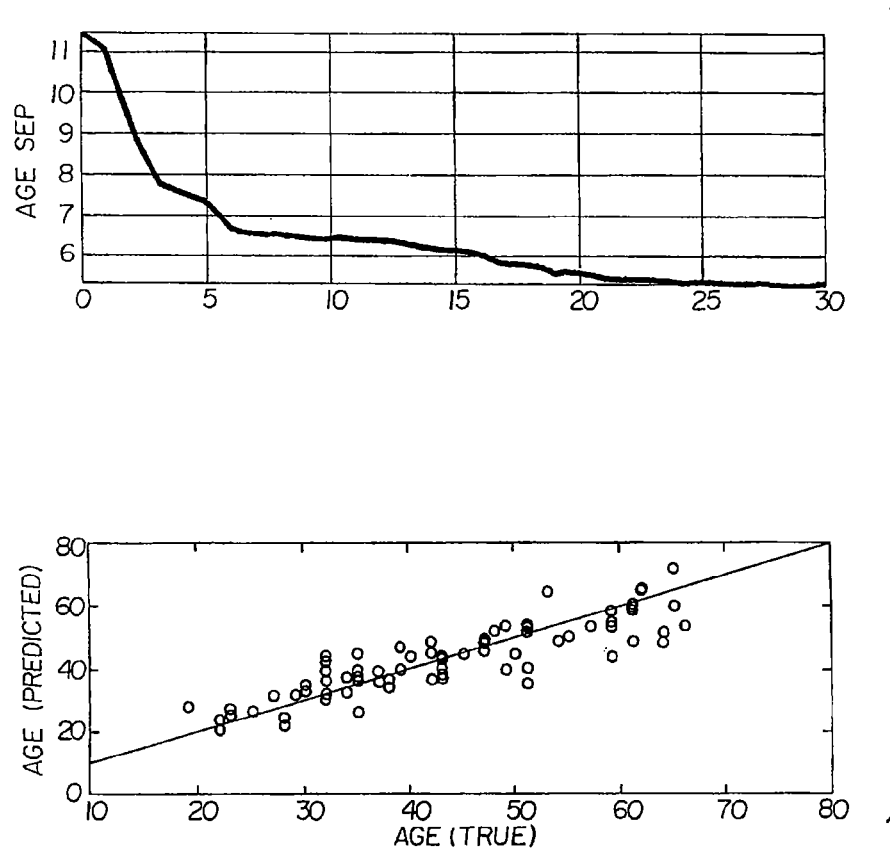
FIG. 14 graphically depicts experimental results for age prediction utilizing an embodiment of the present invention.

The scaled absorbance spectra and the corresponding ages of the subject were used in conjunction with the partial least squares (PLS) multivariate calibration algorithm to determine the age-prediction accuracy. A person-out cross validation was performed, giving the results shown in FIG. 14 where "SEP" is standard error of prediction, which is a one-standard-deviation measure of the error. It can be seen that age predictions with an SEP better than 6 years is possible based upon NIR tissue spectra.

Figure 15:
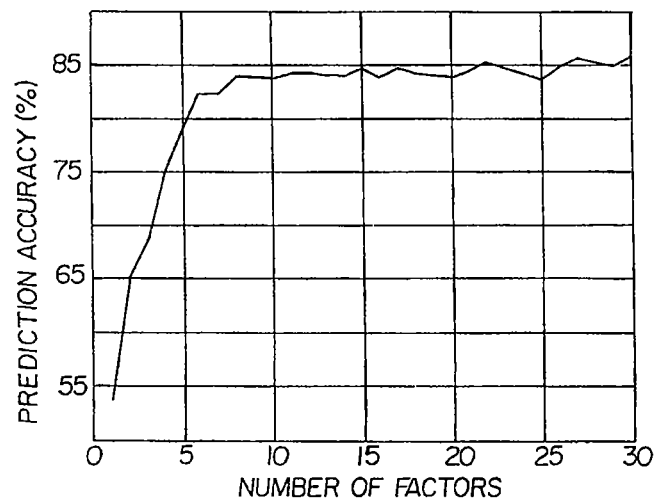
FIG. 15 graphically depicts experimental results for a sex prediction utilizing an embodiment of the present invention.
Figure 16:
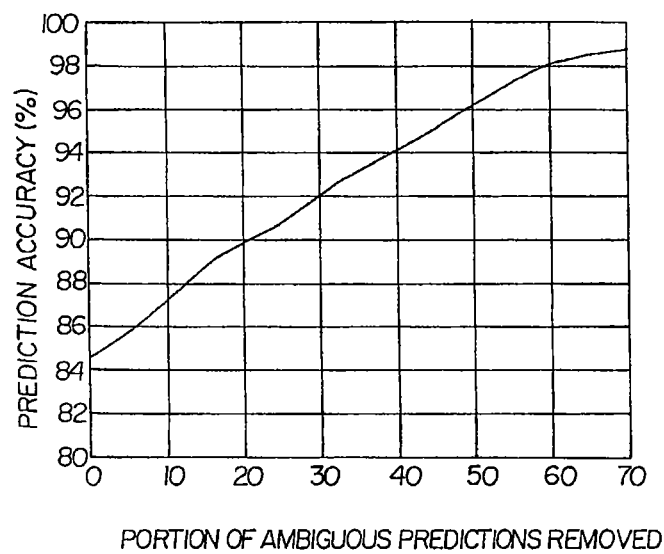
FIG. 16 graphically depicts sex prediction ability versus the portion of data determined to be ambiguous.

A similar multivariate analysis was performed to determine sex prediction capability. In this case, each of the NIR spectra from the 87 subjects was assigned a reference value of either 0 or 1 based upon the sex of the person from whom the spectrum was measured. These spectral data and reference values were then processed using PLS and a subjectout cross-validation to determine sex predictions. Predicted values greater than 0.5 were assigned a value of 1 and predictions less than 0.5 were assigned a 0. The results of this analysis are given in FIG. 15, where it can be seen that approximately 85% of the spectra yielded accurate sex predictions. In some of these cases, the raw predictions were close to the threshold value of 0.5, which implies they were suspect and ambiguous. If those predictions closest to the threshold are eliminated as ambiguous, the prediction ability on the remaining samples is improved. FIG. 16 shows how the prediction ability improves as a function of how often a spectrum is considered ambiguous.

Figure 17:
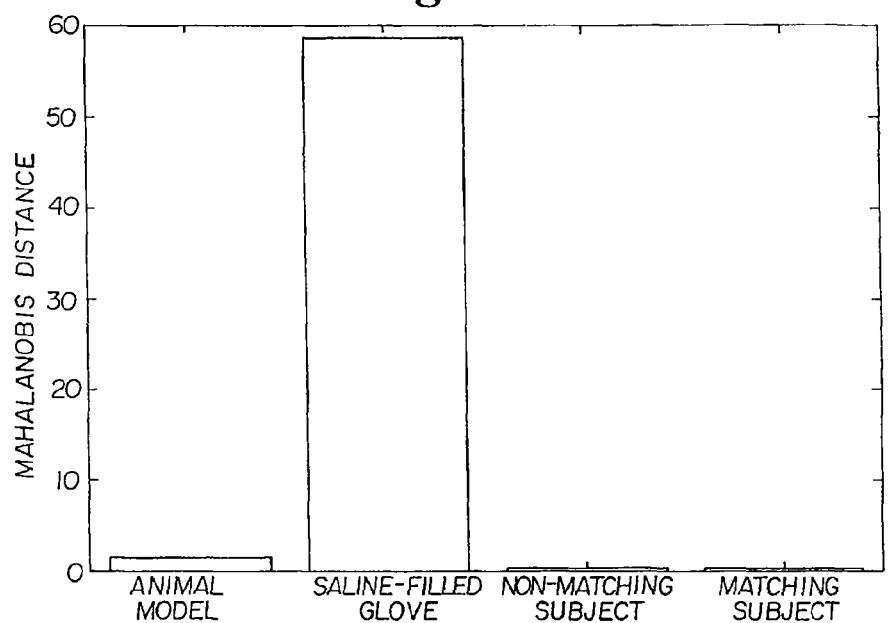
FIG. 17 graphically depicts the results of liveness testing.
Figure 18:
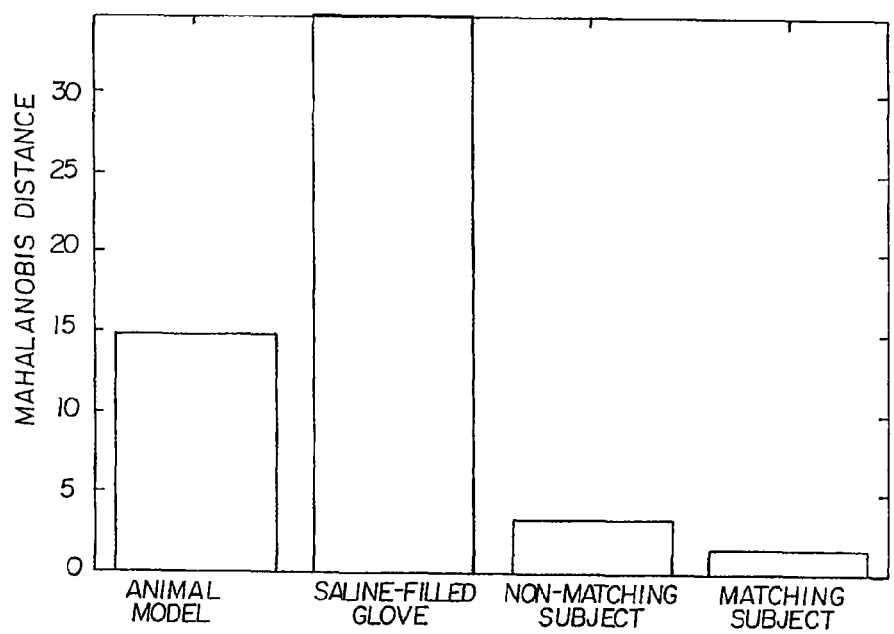
FIG. 18 further details the liveness testing depicted in FIG. 17.

The ability of a spectral biometric to discriminate between live tissue and other sample types is shown in FIGS. 17 and 18. The experiment that gave these results was based on a demonstration that was set up to perform an identification task among a small group of enrolled people. In this experiment, several persons enrolled as valid users on a system similar to the one described in the NIR 87 person analysis section, above. One of the valid users then presented themselves to the system along with another person who was not enrolled in the system. As well, a latex glove was filled with a saline solution and used to collect another test sample. Finally, a piece of cowhide was also measured on the system as a test sample. The results of this experiment are shown in FIG. 17, where it can be seen that the latex glove produces severely inflated matching metrics. FIG. 18 shows a blowup of FIG. 18, where it can also be seen that even a closely matched tissue sample such as the cowhide produces greatly inflated results. The sample taken from the person who is authorized matches best, while the unauthorized person's sample shows a marked inflation relative to the other valid user's sample.

New characteristics and advantages of the invention covered by this document have been set forth in the foregoing description. It will be understood, however, that this disclosure is, in many respects, only illustrative. Changes may be made in details, particularly in matters of shape, size, and arrangement of parts, without exceeding the scope of the invention. The scope of the invention is, of course, defined in the language in which the appended claims are expressed.

What is claimed is:

1. A biometric identification method comprising:
   collecting light from a purported skin site with a light detector embodied in a personal device;
   directing light towards the purported skin site from an illumination source embodied in the personal device;
   detecting linear effects of the collected light to generate a tissue spectrum from the detected linear effects to perform a biometric determination that identifies a sole individual from the tissue spectrum; and
   authorizing access to protected property in accordance with the determination that identifies the sole individual.

2. The biometric identification method of claim 1, wherein emitting light from the illumination source comprises emitting light in a plurality of wavelengths from a plurality of illumination sources.

3. The biometric identification method of claim 1, wherein:
   processing spectral wavelengths comprises:
      comparing the spectral wavelengths to a collection of stored spectral wavelengths; and
      determining whether the spectral wavelengths match at least one of the collection of stored spectral wavelengths; and
   authorizing access to the protected property comprises authorizing access to the protected property based on a determination that the spectral wavelengths match at least one of the collection of stored spectral wavelengths.

4. The biometric identification method of claim 1, wherein the personal device comprises an electronic fob.

5. The biometric identification method of claim 1, wherein the personal device comprises a cellular telephone.

6. The biometric identification method of claim 1, wherein the personal device comprises a wristwatch.

7. The biometric identification method of claim 1, wherein the personal device comprises a smart card.

8. The biometric identification method of claim 1, wherein the personal device comprises a firearm.

9. The biometric identification method of claim 1, wherein the method includes generating, from the collected light, an optical tissue spectrum that includes the spectral wavelengths, wherein the spectral wavelengths contain spectral features that are unique to the sole individual.

10. A biometric identification system, comprising:
    a light detector embodied in a personal device, and configured to collect light from a purported skin site;
    an illumination sources embodied in the personal device, and configured to direct light towards the purported skin site;
    a computational unit having instructions for detecting linear effects of the collected light to generate a tissue spectrum from the detected linear effects to perform a biometric determination that identifies a sole individual from the tissue spectrum and for authorizing access to protected property in accordance with the determination that identifies the sole individual.

11. The biometric identification system of claim 10, wherein the illumination source comprises a plurality of illumination sources embodied in the personal device and configured to emit light in a plurality of wavelengths.

12. The biometric identification system of claim 10, wherein:
    the instructions for processing spectral wavelengths of the collected light comprise:
       instructions for comparing the spectral wavelengths to a collection of stored spectral wavelengths; and
       instructions for determining whether the spectral wavelengths match at least one of the collection of stored spectral wavelengths; and
    the instructions for authorizing access to the protected property comprise instructions for authorizing access to the protected property based on a determination that the spectral wavelengths match at least one of the collection of stored spectral wavelengths.

13. The biometric identification system of claim 10, wherein the personal device comprises an electronic fob.

14. The biometric identification system of claim 10, wherein the personal device comprises a cellular telephone.

15. The biometric identification system of claim 10, wherein the personal device comprises a wristwatch.

16. The biometric identification system of claim 10, wherein the personal device comprises a smart card.

17. The biometric identification system of claim 10, wherein the personal device comprises a firearm.

18. The biometric identification system of claim 10, wherein the computational unit includes instructions for generating, from the collected light, an optical tissue spectrum that includes the spectral wavelengths, wherein the spectral wavelengths contain spectral features that are unique to the sole individual.

\* \* \* \* \*